(12) United States Patent
Sheppard et al.

(10) Patent No.: US 7,135,317 B2
(45) Date of Patent: Nov. 14, 2006

(54) POLYNUCLEOTIDES ENCODING DISINTEGRIN HOMOLOGS, AND RELATED PRODUCTS

(75) Inventors: Paul O. Sheppard, Redmond, WA (US); Nand Baindur, Edmonds, WA (US); Theresa A. Deisher, Seattle, WA (US); Paul D. Bishop, Fall City, WA (US)

(73) Assignee: ZymoGenetics, Inc., Seattle, WA (US)

( * ) Notice: Subject to any disclaimer, the term of this patent is extended or adjusted under 35 U.S.C. 154(b) by 640 days.

(21) Appl. No.: 09/809,617

(22) Filed: Mar. 15, 2001

(65) Prior Publication Data

US 2002/0137178 A1 Sep. 26, 2002

Related U.S. Application Data

(62) Division of application No. 09/351,414, filed on Jul. 9, 1999, now Pat. No. 6,265,199.

(60) Provisional application No. 60/092,371, filed on Jul. 10, 1998.

(51) Int. Cl.
*C12N 9/00* (2006.01)

(52) U.S. Cl. ............... 435/183; 435/320.1; 435/252.3; 536/23.1; 536/23.2

(58) Field of Classification Search ............... 536/23.1, 536/23.2, 28.5; 435/320.1, 252.3, 254.11, 435/325, 419, 226, 183, 69.1
See application file for complete search history.

(56) References Cited

U.S. PATENT DOCUMENTS

2002/0001840 A1 * 1/2002 Lopez-Otin et al.
2002/0042368 A1 * 4/2002 Fanslow et al.

FOREIGN PATENT DOCUMENTS

| JP | 11-155574 A3 * | 6/1999 |
| WO | 97/40072 | 10/1997 |
| WO | WO-99/41388 A2 * | 8/1999 |
| WO | WO-01/62905 A2 * | 8/2001 |
| WO | WO-01/74857 A2 * | 10/2001 |

OTHER PUBLICATIONS

Sagane et al. Metalloproteinase-like, disintegrin-like, cysteine-rich proteins MDC2 and MDC3: novel human cellular disintegrins highly expressed in the brain. Biochem. J. (Aug., 1998) 334:93-98.*
Sagane K. GenBank Accession No. AB009673. Mus musculus mRNA for ADAM23, complete cds. Published Aug. 17, 1999.*
Hochuli et al. Bio/Technology (1988) 11:1321-1325.*
Incyte Pharmaceuticals Inc. EST, LIN305461RI, 1996.
TIGR Tentative Human Consensus THC157294, 1997.
Incyte Pharmaceuticals Inc. EST, INC5314554, 1998.
Hopp, et al., *Proc. Natl. Acad. Sci.* 78: 3824-3828, 1981.
Wolfsberg, et al., *Developmental Biology* 169: 378-383, 1995.
Wolfsberg, et al., *Developmental Biology* 180: 389-401, 1996.
Blobel, *Cell* 90;589-592, 1997.
Jia, et al., *J. Biol. Chem.* 272: 13094-13102, 1997.
Barker, et al., *J. Med. Chem.* 35: 2040-2048, 1992.
Hillier et al., Acc. No. R15038, The Wash U-Merck EST Project, 1995.
Adams, et al., Acc. No. AA317222, 1997.
Hillier et al., Acc. No. R52569.1, The Wash U-Merck EST Project, 1995.
Eisal Co. Ltd. Abstract No. JP11155574, 1999.
Acc. No. AB009672, Entrez, 1998.
Acc. No. AB009671, Entrez, 1998.
Acc No. Z41219, EST68593, 1994.
Acc No. F08148, EST127120, 1995.
Acc. No. R15038, EST185722, The Wash U-Merck EST Project, 1995.
Acc. No. R41476, EST224941, 1995.
Acc. No. R52521, EST222586, 1995.
Acc. No. R52569, EST222634, 1995.
Acc No. AA317222, EST958582, 1997.
Acc. No. AA511039, EST1155679, 1997.
Acc. No. AA718688, EST1425401, 1997.
Acc. No. A1535213, EST2351373, 1999.
Acc. No. A1692184, EST2596722, 1999.
TIGR Tentative human consensus, THC117909, 1997.
TIGR Tentative human consensus, THC108261, 1997.
Incyte Pharmaceuticals Inc. EST, INC2661076, 1997.
LIFESEQ™ Library Information Results LUNGTUT09, Incyte Pharmaceuticals Inc., date unknown.
Incyte Pharmaceuticals Inc. EST, INC2845562, 1997.
LIFESEQ™ Library Information Results DRGLNOT01, Incyte Pharmaceuticals Inc., date unknown.
Incyte Pharmaceuticals Inc. EST, INC3564092, 1997.
LIFESEQ™ Library Information Results SKINNOT05, Incyte Pharmaceuticals Inc., date unknown.
Incyte Pharmaceuticals Inc. EST, INC3859516, 1997.
LIFESEQ™ Library Information Results LNODNOT03, Incyte Pharmaceuticals Inc., date unknown.
Incyte Pharmaceuticals Inc. EST, INC4624120, 1998.
LIFESEQ™ Library Information Results ENDVNOT01, Incyte Pharmaceuticals Inc., date unknown.

(Continued)

*Primary Examiner*—Kathleen Kerr
(74) *Attorney, Agent, or Firm*—Robyn Adams

(57) ABSTRACT

The present invention relates to human polynucleotide and polypeptide molecules for zdint1, a novel member of the Disintegrin Proteases. The polypeptides, and polynucleotides encoding them, are believed to be cell-cell interaction modulating and may be used for delivery and therapeutics. The present invention also includes antibodies to the zdint1 polypeptides.

10 Claims, 17 Drawing Sheets

OTHER PUBLICATIONS

Incyte Pharmaceuticals Inc. EST, INC5095454, 1998.
Incyte Pharmaceuticals Inc. EST, INC5094706, 1998.
LIFESEQ™ Library Information Results EPIMNON05, Incyte Pharmaceuticals Inc., date unknown.
Incyte Pharmaceuticals Inc. EST, INC5849729, 1999.
LIFESEQ™ Library Information Results BRAENOT04, Incyte Pharmaceuticals Inc., date unknown.
Lexicon Pharmaceuticals OST, OST38070, 1998.
Sagane, K. et al., GenBank Accession No. BAA32351, Aug. 14, 1998.
Schwartz, E. et al., GenBank Accession No. CAA52735, Jul. 27, 1994.
Renne, R. et al., GenBank Accession No. VCLJLK, Sep. 9, 1994.
Christiano, A. et al., GenBank Accession No. Q02388, Feb. 15, 2000.
Babel, W. et al., GenBank Accession No. XWBO, Feb. 7, 1997.
Duesterhoeft, A. et al., GenBank Accession No. S39088, Apr. 12, 1996.

* cited by examiner

| | | |
|---|---|---|
| 438 | 1.20 | R========== |
| 439 | 0.53 | D===== |
| 440 | 0.53 | A===== |
| 441 | 0.32 | V=== |
| 442 | 0.50 | N===== |
| 443 | 0.97 | E========= |
| 444 | 0.08 | C= |
| 445 | 0.08 | D= |
| 446 | -0.48 | =====I |
| 447 | -0.18 | ==T |
| 448 | 0.38 | E==== |
| 449 | -0.07 | =Y |
| 450 | 0.32 | C=== |
| 451 | 0.52 | T===== |
| 452 | 0.42 | G==== |
| 453 | 0.42 | D==== |
| 454 | -0.08 | =S |
| 455 | -0.10 | =G |
| 456 | -0.40 | ====Q |
| 457 | -0.52 | =====C |
| 458 | 0.15 | P== |
| 459 | 0.18 | P== |
| 460 | 0.68 | N====== |
| 461 | 0.65 | L====== |
| 462 | 0.57 | H===== |
| 463 | 0.57 | K===== |
| 464 | -0.10 | =Q |
| 465 | -0.10 | =D |
| 466 | -0.57 | ======G |
| 467 | -0.53 | =====Y |
| 468 | -0.12 | =A |
| 469 | -0.03 | C |
| 470 | 0.63 | N====== |
| 471 | 0.43 | Q==== |
| 472 | 0.02 | N |
| 473 | 0.02 | Q |
| 474 | -0.02 | G |
| 475 | 0.48 | R===== |
| 476 | -0.18 | ==C |
| 477 | 0.48 | Y===== |
| 478 | 0.80 | N======= |
| 479 | 1.27 | G=========== |
| 480 | 1.77 | E================ |
| 481 | 1.30 | C=========== |

| | | |
|---|---|---|
| 614 | 0.75 | P======= |
| 615 | 1.25 | L=========== |
| 616 | 1.30 | D=========== |
| 617 | 0.63 | S====== |
| 618 | 0.63 | K====== |
| 619 | 0.13 | G= |
| 620 | 0.05 | K= |
| 621 | -0.45 | =====V |
| 622 | -0.45 | =====C |
| 623 | -0.45 | =====S |
| 624 | -0.45 | =====G |
| 625 | -0.42 | ====H |
| 626 | 0.17 | G== |
| 627 | 0.08 | V= |
| 628 | 0.27 | C=== |
| 629 | 0.27 | S=== |
| 630 | -0.08 | =N |
| 631 | -0.28 | ===E |
| 632 | -0.28 | ===A |
| 633 | -0.62 | ======T |
| 634 | -0.62 | ======C |
| 635 | -1.02 | ==========I |
| 636 | -0.80 | ========C |
| 637 | -0.63 | ======D |
| 638 | -1.20 | ============F |
| 639 | -0.28 | ===T |
| 640 | -0.38 | ====W |
| 641 | 0.23 | A== |
| 642 | 0.02 | G |
| 643 | 0.52 | T===== |
| 644 | 1.08 | D========== |
| 645 | 0.58 | C====== |
| 646 | 0.50 | S===== |
| 647 | 0.95 | I========= |
| 648 | 1.28 | R============ |
| 649 | 0.48 | D===== |
| 650 | -0.10 | =P |
| 651 | -0.10 | =V |
| 652 | 0.15 | R== |
| 653 | 0.15 | N== |
| 654 | 0.62 | L====== |
| 655 | 1.42 | H============= |
| 656 | 1.50 | P============== |
| 657 | 1.50 | P============== |

SEQUENCE LISTING

<160> NUMBER OF SEQ ID NOS: 13

<210> SEQ ID NO 1
<211> LENGTH: 2268
<212> TYPE: DNA
<213> ORGANISM: Homo sapiens
<220> FEATURE:
<221> NAME/KEY: CDS
<222> LOCATION: (3)...(2090)
<221> NAME/KEY: misc_feature
<222> LOCATION: (1)...(2268)
<223> OTHER INFORMATION: n = A,T,C or G

<400> SEQUENCE: 1

```
cc act gtg ttg gaa ttc ggc acg agg ctt gac aca aag gca aga cac        47
   Thr Val Leu Glu Phe Gly Thr Arg Leu Asp Thr Lys Ala Arg His
     1               5                  10                  15 cag caa aaa cat aat aag gct gtc cat ctg gcc cag gca agc ttc cag       95
Gln Gln Lys His Asn Lys Ala Val His Leu Ala Gln Ala Ser Phe Gln
             20                  25                  30 att gaa gcc ttc ggc tcc aaa ttc att ctt gac ctc ata ctg aac aat      143
Ile Glu Ala Phe Gly Ser Lys Phe Ile Leu Asp Leu Ile Leu Asn Asn
         35                  40                  45 ggt ttg ttg tct tct gat tat gtg gag att cac tac gaa aat ggg aaa      191
Gly Leu Leu Ser Ser Asp Tyr Val Glu Ile His Tyr Glu Asn Gly Lys
     50                  55                  60 cca cag tac tct aag ggt gga gag cac tgt tac tac cat gga agc atc      239
Pro Gln Tyr Ser Lys Gly Gly Glu His Cys Tyr Tyr His Gly Ser Ile
 65                  70                  75 aga ggc gtc aaa gac tcc aag gtg gct ctg tca acc tgc aat gga ctt      287
Arg Gly Val Lys Asp Ser Lys Val Ala Leu Ser Thr Cys Asn Gly Leu
 80                  85                  90                  95 cat ggc atg ttt gaa gat gat acc ttc gtg tat atg ata gag cca cta      335
His Gly Met Phe Glu Asp Asp Thr Phe Val Tyr Met Ile Glu Pro Leu
            100                 105                 110
```

```
                                                           -continued gag ctg gtt cat gat gag aaa agc aca ggt cga cca cat ata atc cag      383
Glu Leu Val His Asp Glu Lys Ser Thr Gly Arg Pro His Ile Ile Gln
            115                 120                 125 aaa acc ttg gca gga cag tat tct aag caa atg aag aat ctc act atg      431
Lys Thr Leu Ala Gly Gln Tyr Ser Lys Gln Met Lys Asn Leu Thr Met
130                 135                 140 gaa aga ggt gac cag tgg ccc ttt ctc tct gaa tta cag tgg ttg aaa      479
Glu Arg Gly Asp Gln Trp Pro Phe Leu Ser Glu Leu Gln Trp Leu Lys
    145                 150                 155 aga agg aag aga gca gtg aat cca tca cgt ggt ata ttt gaa gaa atg      527
Arg Arg Lys Arg Ala Val Asn Pro Ser Arg Gly Ile Phe Glu Glu Met
160                 165                 170                 175 aaa tat ttg gaa ctt atg att ggt aat gat cac aaa acg tat aag aag      575
Lys Tyr Leu Glu Leu Met Ile Gly Asn Asp His Lys Thr Tyr Lys Lys
                180                 185                 190 cat cgc tct tct cat gca cat acc aac aac ttt gca aag tcc gtg gtc      623
His Arg Ser Ser His Ala His Thr Asn Asn Phe Ala Lys Ser Val Val
            195                 200                 205 aac ctt gtg gat tct att tac aag gag cag ctc aac acc agg gtt gtc      671
Asn Leu Val Asp Ser Ile Tyr Lys Glu Gln Leu Asn Thr Arg Val Val
        210                 215                 220 ctg gtg gct gta gag acc tgg act gag aag gat cag att gac atc acc      719
Leu Val Ala Val Glu Thr Trp Thr Glu Lys Asp Gln Ile Asp Ile Thr
225                 230                 235 acc aac cct gtg cag atg ctc cat gag ttc tca aaa tac cgg cag cgc      767
Thr Asn Pro Val Gln Met Leu His Glu Phe Ser Lys Tyr Arg Gln Arg
240                 245                 250                 255 att aag cag cat gct gat gct gtg cac ctc atc tcg cgg gtg aca ttt      815
Ile Lys Gln His Ala Asp Ala Val His Leu Ile Ser Arg Val Thr Phe
                260                 265                 270 cac tat aag aga agc agt ctg agt tac ttt gaa ggt gtc tgt tct cgc      863
His Tyr Lys Arg Ser Ser Leu Ser Tyr Phe Glu Gly Val Cys Ser Arg
            275                 280                 285 aca aga gga gtt ggt gtg aat gag tat ggt ctt cca atg gca gtg gca      911
Thr Arg Gly Val Gly Val Asn Glu Tyr Gly Leu Pro Met Ala Val Ala
        290                 295                 300 caa gta tta tcg cag agc ctg gct caa aac ctt gga atc caa tgg gaa      959
Gln Val Leu Ser Gln Ser Leu Ala Gln Asn Leu Gly Ile Gln Trp Glu
305                 310                 315 cct tct agc aga aag cca aaa tgt gac tgc aca gaa tcc tgg ggt ggc     1007
Pro Ser Ser Arg Lys Pro Lys Cys Asp Cys Thr Glu Ser Trp Gly Gly
320                 325                 330                 335 tgc atc atg gag gaa aca ggg gtg tcc cat tct cga aaa ttt tca aag     1055
Cys Ile Met Glu Glu Thr Gly Val Ser His Ser Arg Lys Phe Ser Lys
                340                 345                 350 tgc agc att ttg gag tat aga gac ttt tta cag aga gga ggt gga gcc     1103
Cys Ser Ile Leu Glu Tyr Arg Asp Phe Leu Gln Arg Gly Gly Gly Ala
            355                 360                 365 tgc ctt ttc aac agg cca aca aag cta ttt gag ccc acg gaa tgt gga     1151
Cys Leu Phe Asn Arg Pro Thr Lys Leu Phe Glu Pro Thr Glu Cys Gly
        370                 375                 380 aat gga tac gtg gaa gct ggg gag gag tgt gat tgt ggt ttt cat gtg     1199
Asn Gly Tyr Val Glu Ala Gly Glu Glu Cys Asp Cys Gly Phe His Val
385                 390                 395 gaa tgc tat gga tta tgc tgt aag aaa tgt tcc ctc tcc aac ggg gct     1247
Glu Cys Tyr Gly Leu Cys Cys Lys Lys Cys Ser Leu Ser Asn Gly Ala
400                 405                 410                 415 cac tgc agc gac ggg ccc tgc tgt aac aat acc tca tgt ctt ttt cag     1295
His Cys Ser Asp Gly Pro Cys Cys Asn Asn Thr Ser Cys Leu Phe Gln
            420                 425                 430
```

-continued

| | |
|---|---|
| cca cga ggg tat gaa tgc cgg gat gct gtg aac gag tgt gat att act<br>Pro Arg Gly Tyr Glu Cys Arg Asp Ala Val Asn Glu Cys Asp Ile Thr<br>           435                    440                   445 | 1343 |
| gaa tat tgt act gga gac tct ggt cag tgc cca cca aat ctt cat aag<br>Glu Tyr Cys Thr Gly Asp Ser Gly Gln Cys Pro Pro Asn Leu His Lys<br>450                    455                    460 | 1391 |
| caa gac gga tat gca tgc aat caa aat cag ggc cgc tgc tac aat ggc<br>Gln Asp Gly Tyr Ala Cys Asn Gln Asn Gln Gly Arg Cys Tyr Asn Gly<br>465                    470                    475 | 1439 |
| gag tgc aag acc aga gac aac cag tgt cag tac atc tgg gga aca aag<br>Glu Cys Lys Thr Arg Asp Asn Gln Cys Gln Tyr Ile Trp Gly Thr Lys<br>480                    485                    490                   495 | 1487 |
| gct gca ggg tct gac aag ttc tgc tat gaa aag ctg aat aca gaa ggc<br>Ala Ala Gly Ser Asp Lys Phe Cys Tyr Glu Lys Leu Asn Thr Glu Gly<br>           500                    505                    510 | 1535 |
| act gag aag gga aac tgc ggg aag gat gga gac cgg tgg att cag tgc<br>Thr Glu Lys Gly Asn Cys Gly Lys Asp Gly Asp Arg Trp Ile Gln Cys<br>           515                    520                    525 | 1583 |
| agc aaa cat gat gtg ttc tgt gga ttc tta ctc tgt acc aat ctt act<br>Ser Lys His Asp Val Phe Cys Gly Phe Leu Leu Cys Thr Asn Leu Thr<br>           530                    535                    540 | 1631 |
| cga gct cca cgt att ggt caa ctt cag ggt gag atc att cca act tcc<br>Arg Ala Pro Arg Ile Gly Gln Leu Gln Gly Glu Ile Ile Pro Thr Ser<br>545                    550                    555 | 1679 |
| ttc tac cat caa ggc cgg gtg att gac tgc agt ggt gcc cat gta gtt<br>Phe Tyr His Gln Gly Arg Val Ile Asp Cys Ser Gly Ala His Val Val<br>560                    565                    570                   575 | 1727 |
| tta gat gat gat acg gat gtg ggc tat gta gaa gat gga acg cca tgt<br>Leu Asp Asp Asp Thr Asp Val Gly Tyr Val Glu Asp Gly Thr Pro Cys<br>                     580                    585                   590 | 1775 |
| ggc ccg tct atg atg tgt tta gat cgg aag tgc cta caa att caa gcc<br>Gly Pro Ser Met Met Cys Leu Asp Arg Lys Cys Leu Gln Ile Gln Ala<br>                595                    600                    605 | 1823 |
| cta aat atg agc agc tgt cca ctc gat tcc aag ggt aaa gtc tgt tcg<br>Leu Asn Met Ser Ser Cys Pro Leu Asp Ser Lys Gly Lys Val Cys Ser<br>           610                    615                    620 | 1871 |
| ggc cat ggg gtg tgt agt aat gaa gcc acc tgc att tgt gat ttc acc<br>Gly His Gly Val Cys Ser Asn Glu Ala Thr Cys Ile Cys Asp Phe Thr<br>625                     630                    635 | 1919 |
| tgg gca ggg aca gat tgc agt atc cgg gat cca gtt agg aac ctt cac<br>Trp Ala Gly Thr Asp Cys Ser Ile Arg Asp Pro Val Arg Asn Leu His<br>640                    645                    650                   655 | 1967 |
| ccc ccc aag gat gaa gga ccc aag ggt ttg tgt gat ttt ggt ttc aat<br>Pro Pro Lys Asp Glu Gly Pro Lys Gly Leu Cys Asp Phe Gly Phe Asn<br>           660                    665                    670 | 2015 |
| tca tgg aat act gaa ttc gtt gac act gtt cca atg cac cag tat aac<br>Ser Trp Asn Thr Glu Phe Val Asp Thr Val Pro Met His Gln Tyr Asn<br>               675                    680                   685 | 2063 |
| att cta att gac tta aga gga gac aca taagaatatc ngtttttgcc<br>Ile Leu Ile Asp Leu Arg Gly Asp Thr<br>           690                    695 | 2110 |
| tttaaagtat ataatttatg ttactgccaa attaaggatt ctgatatatc atatttttaa | 2170 |
| aatgtgtttg aattacttct tagtctagaa ctgagattgg gaagaagtaa atatacacat | 2230 |
| tttcttaat acagtattct ttttctcttt aaaccttta | 2268 |

<210> SEQ ID NO 2
<211> LENGTH: 696
<212> TYPE: PRT

<213> ORGANISM: Homo sapiens

<400> SEQUENCE: 2

```
Thr Val Leu Glu Phe Gly Thr Arg Leu Asp Thr Lys Ala Arg His Gln
  1               5                  10                  15
Gln Lys His Asn Lys Ala Val His Leu Ala Gln Ala Ser Phe Gln Ile
             20                  25                  30
Glu Ala Phe Gly Ser Lys Phe Ile Leu Asp Leu Ile Leu Asn Asn Gly
         35                  40                  45
Leu Leu Ser Ser Asp Tyr Val Glu Ile His Tyr Glu Asn Gly Lys Pro
     50                  55                  60
Gln Tyr Ser Lys Gly Gly Glu His Cys Tyr Tyr His Gly Ser Ile Arg
 65                  70                  75                  80
Gly Val Lys Asp Ser Lys Val Ala Leu Ser Thr Cys Asn Gly Leu His
                 85                  90                  95
Gly Met Phe Glu Asp Asp Thr Phe Val Tyr Met Ile Glu Pro Leu Glu
            100                 105                 110
Leu Val His Asp Glu Lys Ser Thr Gly Arg Pro His Ile Ile Gln Lys
        115                 120                 125
Thr Leu Ala Gly Gln Tyr Ser Lys Gln Met Lys Asn Leu Thr Met Glu
    130                 135                 140
Arg Gly Asp Gln Trp Pro Phe Leu Ser Glu Leu Gln Trp Leu Lys Arg
145                 150                 155                 160
Arg Lys Arg Ala Val Asn Pro Ser Arg Gly Ile Phe Glu Glu Met Lys
                165                 170                 175
Tyr Leu Glu Leu Met Ile Gly Asn Asp His Lys Thr Tyr Lys Lys His
            180                 185                 190
Arg Ser Ser His Ala His Thr Asn Asn Phe Ala Lys Ser Val Val Asn
        195                 200                 205
Leu Val Asp Ser Ile Tyr Lys Glu Gln Leu Asn Thr Arg Val Val Leu
    210                 215                 220
Val Ala Val Glu Thr Trp Thr Glu Lys Asp Gln Ile Asp Ile Thr Thr
225                 230                 235                 240
Asn Pro Val Gln Met Leu His Glu Phe Ser Lys Tyr Arg Gln Arg Ile
                245                 250                 255
Lys Gln His Ala Asp Ala Val His Leu Ile Ser Arg Val Thr Phe His
            260                 265                 270
Tyr Lys Arg Ser Ser Leu Ser Tyr Phe Glu Gly Val Cys Ser Arg Thr
        275                 280                 285
Arg Gly Val Gly Val Asn Glu Tyr Gly Leu Pro Met Ala Val Ala Gln
    290                 295                 300
Val Leu Ser Gln Ser Leu Ala Gln Asn Leu Gly Ile Gln Trp Glu Pro
305                 310                 315                 320
Ser Ser Arg Lys Pro Lys Cys Asp Cys Thr Glu Ser Trp Gly Gly Cys
                325                 330                 335
Ile Met Glu Glu Thr Gly Val Ser His Ser Arg Lys Phe Ser Lys Cys
            340                 345                 350
Ser Ile Leu Glu Tyr Arg Asp Phe Leu Gln Arg Gly Gly Gly Ala Cys
        355                 360                 365
Leu Phe Asn Arg Pro Thr Lys Leu Phe Glu Pro Thr Glu Cys Gly Asn
    370                 375                 380
Gly Tyr Val Glu Ala Gly Glu Glu Cys Asp Cys Gly Phe His Val Glu
385                 390                 395                 400
```

-continued

```
Cys Tyr Gly Leu Cys Cys Lys Lys Cys Ser Leu Ser Asn Gly Ala His
                405                 410                 415
Cys Ser Asp Gly Pro Cys Cys Asn Asn Thr Ser Cys Leu Phe Gln Pro
            420                 425                 430
Arg Gly Tyr Glu Cys Arg Asp Ala Val Asn Glu Cys Asp Ile Thr Glu
        435                 440                 445
Tyr Cys Thr Gly Asp Ser Gly Gln Cys Pro Pro Asn Leu His Lys Gln
    450                 455                 460
Asp Gly Tyr Ala Cys Asn Gln Asn Gly Arg Cys Tyr Asn Gly Glu
465                 470                 475                 480
Cys Lys Thr Arg Asp Asn Gln Cys Gln Tyr Ile Trp Gly Thr Lys Ala
                485                 490                 495
Ala Gly Ser Asp Lys Phe Cys Tyr Glu Lys Leu Asn Thr Glu Gly Thr
            500                 505                 510
Glu Lys Gly Asn Cys Gly Lys Asp Gly Asp Arg Trp Ile Gln Cys Ser
        515                 520                 525
Lys His Asp Val Phe Cys Gly Phe Leu Leu Cys Thr Asn Leu Thr Arg
    530                 535                 540
Ala Pro Arg Ile Gly Gln Leu Gln Gly Glu Ile Ile Pro Thr Ser Phe
545                 550                 555                 560
Tyr His Gln Gly Arg Val Ile Asp Cys Ser Gly Ala His Val Val Leu
                565                 570                 575
Asp Asp Asp Thr Asp Val Gly Tyr Val Glu Asp Gly Thr Pro Cys Gly
            580                 585                 590
Pro Ser Met Met Cys Leu Asp Arg Lys Cys Leu Gln Ile Gln Ala Leu
        595                 600                 605
Asn Met Ser Ser Cys Pro Leu Asp Ser Lys Gly Lys Val Cys Ser Gly
    610                 615                 620
His Gly Val Cys Ser Asn Glu Ala Thr Cys Ile Cys Asp Phe Thr Trp
625                 630                 635                 640
Ala Gly Thr Asp Cys Ser Ile Arg Asp Pro Val Arg Asn Leu His Pro
                645                 650                 655
Pro Lys Asp Glu Gly Pro Lys Gly Leu Cys Asp Phe Gly Phe Asn Ser
            660                 665                 670
Trp Asn Thr Glu Phe Val Asp Thr Val Pro Met His Gln Tyr Asn Ile
        675                 680                 685
Leu Ile Asp Leu Arg Gly Asp Thr
    690                 695

<210> SEQ ID NO 3
<211> LENGTH: 2088
<212> TYPE: DNA
<213> ORGANISM: Artificial Sequence
<220> FEATURE:
<223> OTHER INFORMATION: zdint1 amino acid degenerate sequence
<221> NAME/KEY: variation
<222> LOCATION: (1)...(2088)
<223> OTHER INFORMATION: n is any nucleotide
<221> NAME/KEY: misc_feature
<222> LOCATION: (1)...(2088)
<223> OTHER INFORMATION: n = A,T,C or G

<400> SEQUENCE: 3
acngtnytng   arttyggnac   nmgnytngay   acnaargcnm   gncaycarca   raarcayaay    60
aargcngtnc   ayytngcnca   rgcnwsntty   carathgarg   cnttyggnws   naarttyath   120
ytngayytna   thytnaayaa   yggnytnytn   wsnwsngayt   aygtngarat   hcaytaygar   180
```

| | |
|---|---|
| aayggnaarc cncartayws naarggnggn garcaytgyt aytaycaygg nwsnathmgn | 240 |
| ggngtnaarg aywsnaargt ngcnytnwsn acntgyaayg gnytncaygg natgttygar | 300 |
| gaygayacnt tygtntayat gathgarccn ytngarytng tncaygayga raarwsnacn | 360 |
| ggnmgnccnc ayathathca raaracnytn gcnggncart aywsnaarca ratgaaraay | 420 |
| ytnacnatgg armgnggnga ycartggccn ttyytnwsng arytncartg gytnaarmgn | 480 |
| mgnaarmgng cngtnaaycc nwsnmgnggn athttygarg aratgaarta yytngarytn | 540 |
| atgathggna aygaycayaa racntayaar aarcaymgnw snwsncaygc ncayacnaay | 600 |
| aayttygcna arwsngtngt naayytngtn gaywsnatht ayaargarca rytnaayacn | 660 |
| mgngtngtny tngtngcngt ngaracntgg acngaraarg aycarathga yathacnacn | 720 |
| aayccngtnc aratgytnca ygarttywsn aartaymgnc armgnathaa rcarcaygcn | 780 |
| gaygcngtnc ayytnathws nmgngtnacn ttycaytaya armgnwsnws nytnwsntay | 840 |
| ttygarggng tntgywsnmg nacnmgnggn gtnggngtna aygartaygg nytnccnatg | 900 |
| gcngtngcnc argtnytnws ncarwsnytn gcncaraayy tnggnathca rtgggarccn | 960 |
| wsnwsnmgna arccnaartg ygaytgyacn garwsntgg

```
<212> TYPE: DNA
<213> ORGANISM: Artificial Sequence
<220> FEATURE:
<223> OTHER INFORMATION: oligonucleotide ZC17992

<400> SEQUENCE: 5
actgaccaga gtctcccagt aca                                              23

<210> SEQ ID NO 6
<211> LENGTH: 20
<212> TYPE: DNA
<213> ORGANISM: Artificial Sequence
<220> FEATURE:
<223> OTHER INFORMATION: oligonucleotide: ZC13006

<400> SEQUENCE: 6
ggctgtcctc taagcgtcac                                                  20

<210> SEQ ID NO 7
<211> LENGTH: 6
<212> TYPE: PRT
<213> ORGANISM: Artificial Sequence
<220> FEATURE:
<223> OTHER INFORMATION: antigenic peptide

<400> SEQUENCE: 7

Lys Arg Arg Lys Arg Ala
1               5

<210> SEQ ID NO 8
<211> LENGTH: 6
<212> TYPE: PRT
<213> ORGANISM: Artificial Sequence
<220> FEATURE:
<223> OTHER INFORMATION: antigenic peptide

<400> SEQUENCE: 8

Leu Lys Arg Arg Lys Arg
1               5

<210> SEQ ID NO 9
<211> LENGTH: 6
<212> TYPE: PRT
<213> ORGANISM: Artificial Sequence
<220> FEATURE:
<223> OTHER INFORMATION: antigenic peptide

<400> SEQUENCE: 9

Gly Lys Asp Gly Asp Arg
1               5

<210> SEQ ID NO 10
<211> LENGTH: 6
<212> TYPE: PRT
<213> ORGANISM: Artificial Sequence
<220> FEATURE:
<223> OTHER INFORMATION: antigenic peptide

<400> SEQUENCE: 10

Lys Asp Glu Gly Pro Lys
1               5

<210> SEQ ID NO 11
<211> LENGTH: 6
<212> TYPE: PRT
<213> ORGANISM: Artificial Sequence
<220> FEATURE:
```

```
-continued

<223> OTHER INFORMATION: antigenic peptide

<400> SEQUENCE: 11

Lys Lys His Arg Ser Ser
1               5

<210> SEQ ID NO 12
<211> LENGTH: 18
<212> TYPE: DNA
<213> ORGANISM: Artificial Sequence
<220> FEATURE:
<223> OTHER INFORMATION: oligonucleotide primer ZC20,843

<400> SEQUENCE: 12
tcctggtggc tgtagaga                                              18

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer ZC20,844

<400> SEQUENCE: 13
tgccggtatt ttgagaac                                              18
```

POLYNUCLEOTIDES ENCODING DISINTEGRIN HOMOLOGS, AND RELATED PRODUCTS

REFERENCE TO RELATED APPLICATIONS

This is a divisional application of application Ser. No. 09/351,414 filed Jul. 9, 1999 now U.S. Pat. No. 6,265,199. This application is related to Provisional Application No. 60/092,371 filed on Jul. 10, 1998. Under 35 U.S.C. § 119(e)(1), this application claims benefit of said Provisional Application.

BACKGROUND OF THE INVENTION

Disintegrins have been shown to bind cell surface molecules, including integrins, on the surface of various cells, such as platelets, fibroblasts, tumor, endothelial, muscle, neuronal, bone, and sperm cells. Disintegrins are unique and potentially useful tools for investigating cell-matrix and cell-cell interactions. Additionally, they have been useful in the development of antithrombotic and antimetastatic agents due to their anti-adhesive, anti-migration of certain tumor cells, and antiangiogenesis activities.

Families of proteins which have disintegrin domains include ADAMs (A Metalloprotease and Disintegrin), MDCs (Metalloprotease/Disintegrin/Cysteine-rich) and SVMPs (Snake Venom Metalloprotease).

For a review of ADAMs, see Wolfsberg and White, *Developmental Biology,* 180:389–401, 1996. ADAMs have been shown to exist as independent functional units or in conjunction with other members of this family in heterodimeric complexes. Some members of the family exist in multiple isoforms which may have resulted from alternative splicing. ADAMs proteins have been shown to have adhesive as well as anti-adhesive functions. Some members of the ADAMs family have very specific tissue distribution while others are widely distributed. Not all members of this family are capable of manifesting all of the potential functions represented by the domains common to their genetic structure.

The ADAMs are characterized by having a propeptide domain, a metalloprotease-like domain, a disintegrin-like domain, a cysteine-rich domain, an EGF-like domain, and a cytoplasmic domain.

A prototypical example of this family is ADAM 12. ADAM 12, also known as meltrin α, has a truncated isoform, as well as a full-length isoform, and is involved in muscle cell fusion and differentiation (Gilpin et al., *J. Biol. Chem.* 273:157–166, 1998).

Another prototypical example of this family is ADAM 1, which forms a heterodimer with ADAM 2 and is involved in sperm/egg fusion (Wolfsberg and White, supra).

The SVMP family is represented by three classes (P-I, P-II, and P-III). All three classes contain propeptide and metalloprotease domains. The P-II and P-III classes also contain a disintegrin domain, and the P-III class further contains a cysteine-rich domain. These domains are similar in sequence to those found in the ADAMs. Some members of the SVMP family have a conserved "RGD" amino acid sequence. This tripeptide has been shown to form a hairpin loop whose conformation can disrupt the binding of fibrinogen to activated platelets. This RGD sequence may be substituted by RSE, MVD, MSE, and KGD in P-II SVMPs, and by MSEC, RSEC, IDDC, and RDDC (a tripeptide along with a carboxy-terminal cysteine residue) in P-III SVMPs. Thus, these sequences may be responsible for integrin binding in the P-II and P-III SVMPs.

A prototypical example of a SVMP is jararhagin, which mediates platelet aggregation by binding to the platelet $\alpha_2$ subunit (GPIa) via the disintegrin domain followed by proteolysis of the $\beta_1$ subunit (GPIIA) (Huang and Liu, *J. Toxicol-Toxin Reviews* 16: 135–161, 1997).

The proteins of the Metalloprotease/Disintegrin/Cysteine-rich family are involved in diverse tasks, ranging from roles in fertilization and muscle fusion, TNFα release from plasma membranes, intracellular protein cleavage, and essential functions in neuronal development (Blobel, *Cell* 90:589–592, 1997). This family is also characterized by the metalloprotease, disintegrin and cysteine-rich domains, as described above.

The present invention provides a novel disintegrin homolog and related compositions whose uses should be apparent to those skilled in the art from the teachings herein.

SUMMARY OF THE INVENTION

Within one aspect, the present invention provides an isolated polypeptide molecule comprising a contiguous sequence of 14 amino acids of SEQ ID NO:2. Within an embodiment the polypeptide molecule comprises residues 437 to 450 of SEQ ID NO:2. Within another embodiment, the polypeptide molecule is between 82 and 232 amino acids in length. Within further embodiments polypeptide molecule is residues 164 to 382 of SEQ ID NO:2; residues 383 to 464 of SEQ ID NO:2; and/or residues 465 to 696 of SEQ ID NO:2.

Within another aspect, the invention provides an isolated polypeptide molecule selected from the group consisting of: a) a polypeptide molecule comprising residues 164 to 382 of SEQ ID NO:2; b) a polypeptide molecule comprising residues 383 to 464 of SEQ ID NO:2; c) a polypeptide molecule comprising residues 465 to 696 of SEQ ID NO:2; d) a polypeptide molecule comprising residues 438 to 449 of SEQ ID NO:2; e) a polypeptide molecule comprising residues 164 to 464 of SEQ ID NO:2; f) a polypeptide molecule comprising residues 164 to 696 of SEQ ID NO:2; g) a polypeptide molecule comprising residues 383 to 696 of SEQ ID NO:2; h) a polypeptide molecule comprising residues 164 to 449 of SEQ ID NO:2; i) a polypeptide molecule comprising residues 438 to 696 of SEQ ID NO:2; and j) a polypeptide molecule comprising residues 1 to 696 of SEQ ID NO:2.

Within another aspect is provided an isolated polynucleotide molecule encoding a polypeptide molecule, wherein the polypeptide molecule comprises a contiguous sequence of 14 amino acids of SEQ ID NO:2. Within an embodiment, the polypeptide molecule comprises residues 437 to 450 of SEQ ID NO:2. Within a further embodiment, the polypeptide molecule is between 82 and 232 amino acids in length. Within further embodiments, the polypeptide molecule is residues 164 to 382 of SEQ ID NO:2; residues 383 to 464 of SEQ ID NO:2; and/or residues 465 to 696 of SEQ ID NO:2.

Within another aspect, the invention provides an isolated polynucleotide molecule encoding a polypeptide molecule, wherein the polypeptide molecule is selected from the group consisting of: a) a polypeptide molecule comprising residues 164 to 382 of SEQ ID NO:2; b) a polypeptide molecule comprising residues 383 to 464 of SEQ ID NO:2; c) a polypeptide molecule comprising residues 465 to 696 of SEQ ID NO:2; d) a polypeptide molecule comprising residues 438 to 449 of SEQ ID NO:2; e) a polypeptide molecule comprising residues 164 to 464 of SEQ ID NO:2; f) a polypeptide molecule comprising residues 164 to 696 of SEQ ID NO:2; g) a polypeptide molecule comprising residues 383 to 696 of SEQ ID NO:2; h) a polypeptide molecule comprising residues 164 to 449 of SEQ ID NO:2; i) a polypeptide molecule comprising residues 438 to 696 of SEQ ID NO:2; and j) a polypeptide molecule comprising residues 1 to 696 of SEQ ID NO:2.

Within another aspect is provided an isolated polynucleotide encoding a fusion protein having a first segment and a second segment, wherein the first segment comprises a first polypeptide encoding a polypeptide having a protease domain and the second segment comprises a second polynucleotide encoding a polypeptide that has a contiguous sequence of 14 amino acids between residues 383 and 464 of SEQ ID NO:2, and wherein the first segment is positioned amino-terminally to the second segment. Within an embodiment, the protease domain is selected from the group consisting of; a) a protease domain that is a member of the Disintegrin Proteases; and b) a protease domain that is at least 80% identical to amino acid residues 164 to 382 of SEQ ID NO:2.

Within another aspect the invention provides an isolated polynucleotide molecule encoding a polypeptide molecule wherein the polynucleotide molecule is selected from the group consisting of: a) a polynucleotide molecule that encodes a polypeptide molecule that is at least 80% identical to residues 383 to 464 of SEQ ID NO:2; and b) a polynucleotide molecule that is complementary to a). Within an embodiment, the polynucleotide molecule is selected from the group consisting of: a) a polynucleotide molecule that encodes a polypeptide molecule that is at least 80% identical to residues 383 to 696 of SEQ ID NO:2; and b) a polynucleotide molecule that is complementary to a). Within a further embodiment, the polynucleotide molecule is selected from the group consisting of: a) a polynucleotide molecule that encodes a polypeptide molecule that is at least 80% identical to residues 1 to 696 of SEQ ID NO:2; and b) a polynucleotide molecule that is complementary to a).

Within another aspect is provided an expression vector comprising the following operably linked elements: a) a transcription promoter; b) a DNA segment encoding the polypeptide of claim 1; and c) a transcription terminator. Within an embodiment the DNA segment further encodes an affinity tag.

Within another aspect, the invention provides a cultured cell into which has been introduced said expression vector, wherein the cell expresses the polypeptide encoded by the DNA segment.

Within another aspect, the invention provides a method of producing a polypeptide comprising culturing the cell expressing the polypeptide encoded by the DNA segment; and recovering the polypeptide.

Within another aspect is provided a method for modulating cell-cell interactions by combining the polypeptide comprising the sequence of 14 contiguous amino acids, with cells in vivo and in vitro. Within an embodiment, the cells are derived from tissues selected from the group consisting of: a) tissues from heart; b) tissues from brain; c) tissues from spinal cord; and d) tissues from skeletal muscle.

Within another aspect, the invention provides an isolated polypeptide molecule comprising a contiguous sequence of amino acids, wherein the contiguous sequence of amino acids is selected from the group consisting of: a) SEQ ID NO:7; b) SEQ ID NO:8; c) SEQ ID NO:9; d) SEQ ID NO:10; and e) SEQ ID NO:11.

Within another aspect is provide an isolated polynucleotide molecule encoding an isolated polypeptide molecule, wherein the polypeptide comprises a contiguous sequence of amino acids and is selected from the group consisting of: a) SEQ ID NO:7; b) SEQ ID NO:8; c) SEQ ID NO:9; d) SEQ ID NO:10; and e) SEQ ID NO:11.

These and other aspects of the invention will become evident upon reference to the following detailed description of the invention and attached drawings.

DETAILED DESCRIPTION OF THE INVENTION

Figure 1A:
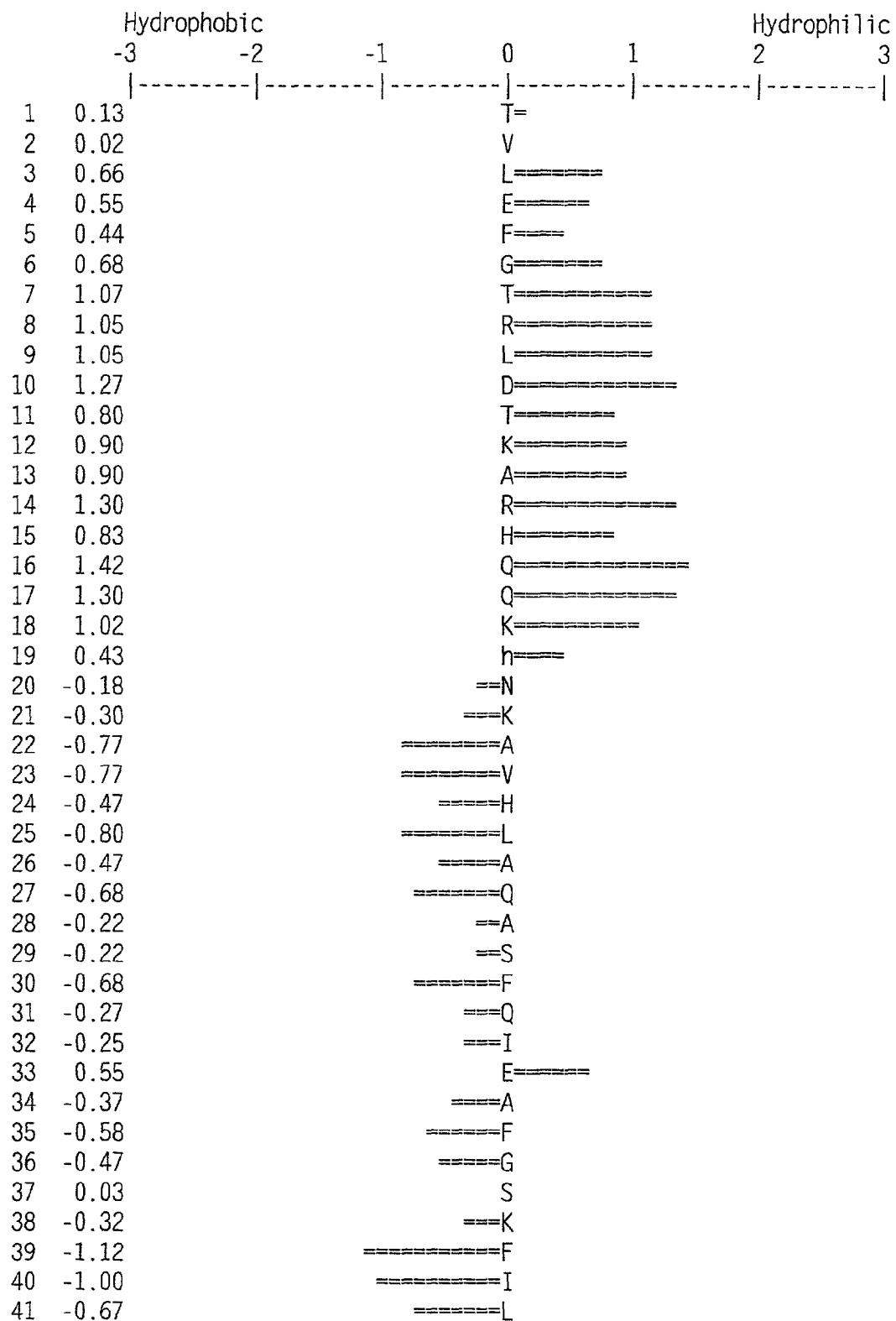
FIG. 1 is a Hopp/Woods hydrophilicity profile of the zdint1 protein sequence shown in SEQ ID NO:2. The profile is based on a sliding six-residue window. Buried G, S, and T residues and exposed H, Y, and W residues were ignored. These residues are indicated in the figure by lower case letters.
Figure 1P:
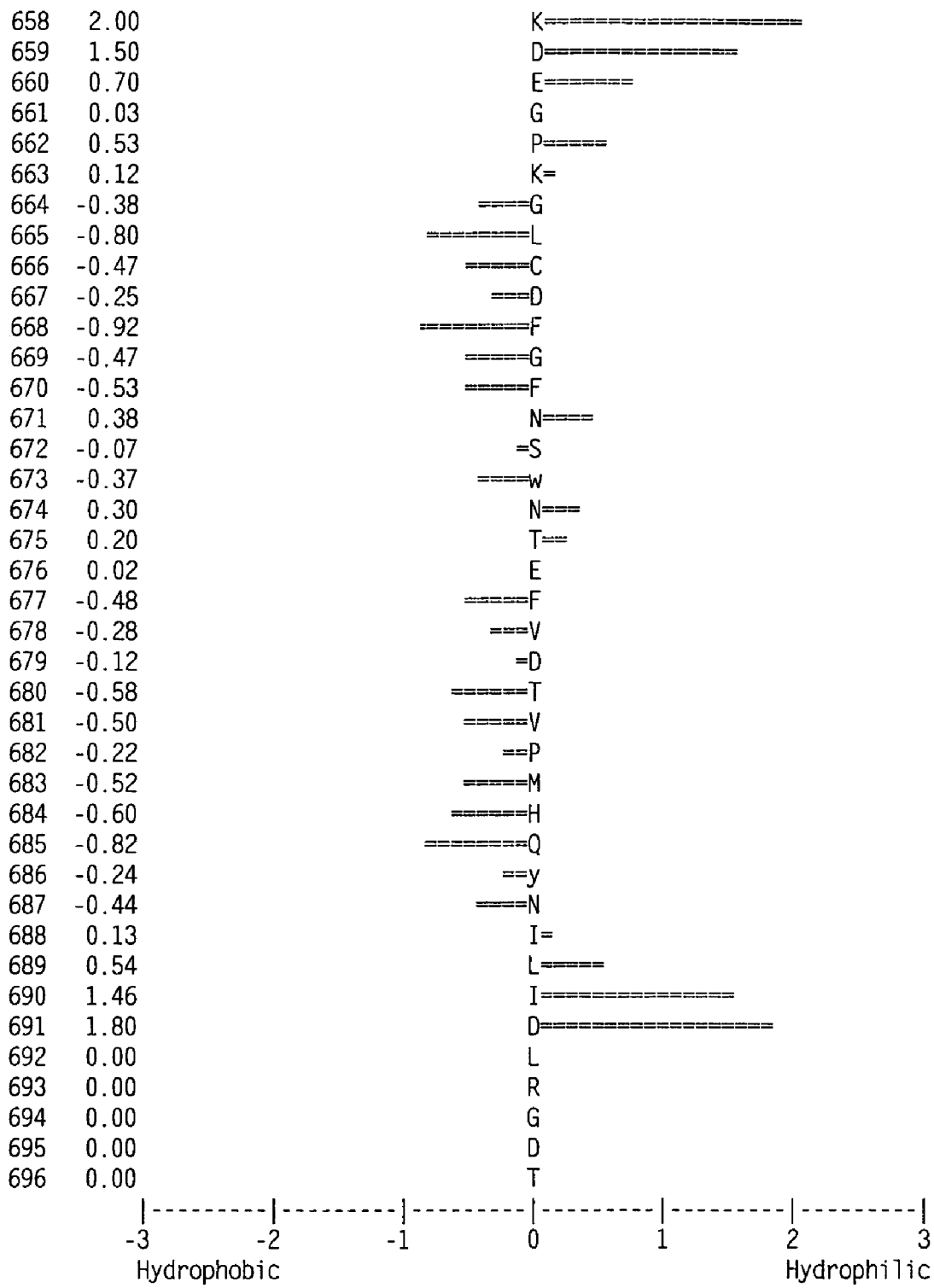
Figure 2:
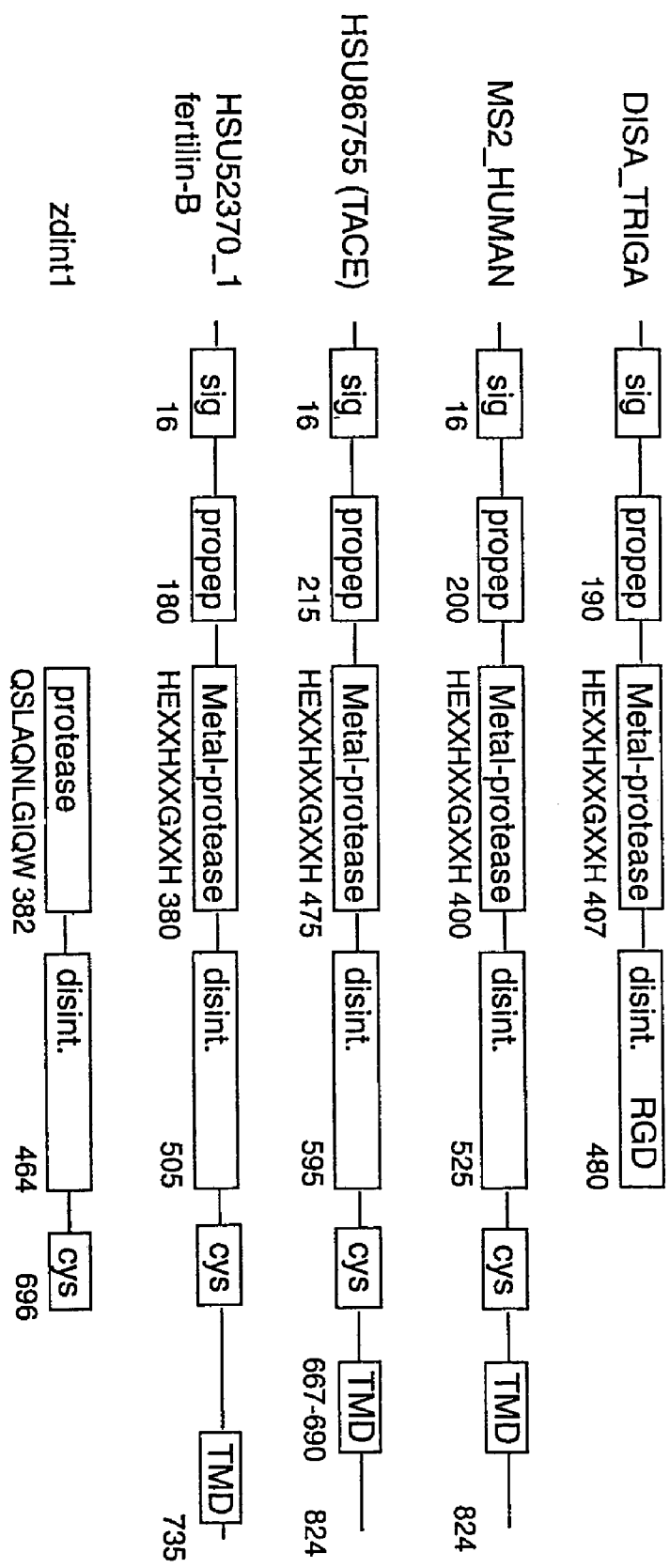
FIG. 2 schematically shows a domain level alignment of members of ADAMs, MDCs, and SVMPs. DISA_TRIGA is a SVMP. MS2_HUMAN is an ADAM. HSUTSP1 (TACE) is a MDC. And HSU52370_1 is fertilin-β, ADAM 2. "sig" denotes the secretory signal peptide; "propep" denotes the propeptide domain; "Metal-protease" denotes the metalloprotease domain; "disint" denotes the disintegrin domain; "cys" denotes the cysteine-rich domain; "RGD" denotes a tripeptide, Arginine-Glycine-Asparagine; and "TMD" denotes the transmembrane domain.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGAGCTT-3' are 5'-AGCTTgagt-3' and 3'-tcgacTACC-5'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, a-globin, b-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules, it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus, all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based upon the discovery of a novel cDNA sequence (SEQ ID NO:1) and corresponding polypeptide (SEQ ID NO:2) having homology to disintegrin-like family members (ADAMs, SVMPs and MDCs; referred to herein as Disintegrin Proteases, or "DPs"). See, for example, Blobel, *Cell* 90:589–592, 1997, and Wolfsberg and White, *Developmental Biology* 180:389–401, 1996. Disintegrins can be involved in, for example, anticoagulation, fertilization, muscle fusion, connective tissue disorders, chondrogenesis, arthritis, metastasis and neurogenesis.

The secretory signal (also known as a leader sequence, prepro sequence or pre sequence) domain of these polypeptides directs the polypeptide through a secretory pathway of a cell in which it is synthesized. The secretory signal and propeptide domain are cleaved from the full length molecule, resulting in the mature form of the zdint1 polypeptide. The protease domain may be active or inactive. Some members of the disintegrin family have "active" zinc catalytic sites which may be regulated by a "cysteine-switch" in the cysteine-rich domain. Examples of family members which have "active" protease domains are ADAM 1 and ADAM 10, which are involved in sperm/egg fusion and degradation of myelin basic sheath protein, respectively. Other members of this family do not have such a catalytic site and are "inactive". An example of a family member which contains an inactive protease domain is ADAM 11, which may be involved in tumor suppression. Other protein families which are known to have inactive protease domains are the serine proteases.

The adhesion (disintegrin) domain of this protein binds integrin domains on the surface a multitude of cells, depending on the specificity of the disintegrin. The predicted binding site within this disintegrin domain is often an amino acid loop comprising about 13 amino acids. The conformation of this sequence upon folding results in a hairpin loop presenting an amino acid sequence at its tip. This sequence is often "RGD", but may be substituted by a variety of other amino acid residues (Wolfsberg and White, supra; and Jia, *J. Biol. Chem.* 272:13094–13102 1997). The diversity of these sequences may reflect that: 1) not all disintegrin domains serve as ligands for integrins (or other cell surface receptors); 2) disintegrin domains with different sequences bind to different types of cell surface receptors; or 3) the important part of the disintegrin structure loop is its structure, not its sequence, and thus, that the receptors for the specific classes of disintegrin domains can recognize a multitude of disintegrin binding loop sequences. Disintegrin domains have been shown to be responsible for cell-cell interactions, including inhibition of platelet aggregation by binding GPIIb/IIIa (fibronectin receptor) and/or GPIa/IIa (collagen receptor) as well as cell fusion.

Many disintegrin family members have a fusion domain, a relatively hydrophobic domain of about 23 amino acids. This domain is present within some of the ADAM family members, and has been shown to be involved in cell-cell fusion, and particularly in sperm/egg fusion, and muscle fusion.

The cysteine-rich domain varies in the DP family members and is believed to be involved in structurally presenting the integrin-binding region to integrins.

Many DP family members have a transmembrane domain, which acts to anchor the polypeptide to the cell membrane.

The signaling domain of disintegrin family members tends to be conserved in length and sites for phosphorylation. However, beyond that they tend to be unique in amino acid composition. Some disintegrin family members may signal by binding to the SH3 domain of Abl, Src, and/or Src-related SH3 domains.

The zdint1 polypeptides of the present invention are a novel member of the DP family. The presence of isoforms of zdint1 which also comprise a transmembrane domain would suggest that zdint1 will have an alternatively spliced variant with a signaling domain.

The novel zdint1 polypeptide-encoding polynucleotides of the present invention were initially identified by performing a Blast similarity search. An expressed sequence tag corresponding to nucleotides 1097 to 1415 of SEQ ID NO:1 was used to obtain a clone that had been isolated from an infant brain plasmid library.

Examination of the zdint1 deduced amino acid sequence (SEQ ID NO:2) permitted identification of the following domains: a propeptide sequence, ending at residue 163 of SEQ ID NO: 2; a protease sequence, residues 164 to 382 of SEQ ID NO: 2; a disintegrin sequence, residues 383 to 464 of SEQ ID NO: 2; and a cysteine-rich sequence, residues 465 to 696 of SEQ ID NO:2. Within the disintegrin domain, there is a "disintegrin loop" sequence, residues 438 to 449 of SEQ ID NO:2. The amino acid sequence, ECD, which corresponds to residues 443 to 445 of SEQ ID NO: 2, is analogous to the "RGD binding loop" of some other members of the DPs.

Analysis of tissue distribution of zdint1 was performed by the Northern blotting technique using Human Multiple Tissue, Master Dot, and human vascular blots. Strong signals of three transcript sizes, approximately 3.0 kb, 4.4 kb, and 7.5 kb, were observed in heart on the multiple tissue Northern blots. Faint signals of the same transcript sizes were observed in brain and spinal cord. Fainter signals of the three transcript sizes were observed in skeletal muscle. The Master Dot Blot showed strong signals in brain, heart, fetal brain, and fetal heart. The human vascular blot showed a strong signal at 3–3.5 kb in human aortic endothelial cells and weaker signals in aortic smooth muscle cells and normal human lung fibroblast cells.

The protease domain of zdint1 has 49.5% identity to the protease domain of the nearest family neighbor, ADAM 11, at the polypeptide level, and 58% identity at the polynucleotide level. The disintegrin domain of zdint1 has 66.7% identity to the disintegrin domain of the nearest family neighbor, ADAM 11, at the polypeptide level, and 64.3% identity at the polynucleotide level. The expression of ADAM 11 has been shown to decrease in breast cancer tissues and, thus, is suggested to act as a tumor suppresser in breast cancer (Emi et al., *Nature Gen.* 5:151–157, 1993). Additionally, ADAM 11 has been shown to have multiple isoforms as a result of alternative splicing.

Another protein which is an example of alternative splicing in the DPs is ADAM 12, meltrin α. The truncated form of this molecule, which lacks the propeptide and metalloprotease domains, is associated with ectopic muscle formation in vivo, but not in vitro, indicating that cells expressing this gene produce a growth factor that acts on neighboring progenitor cells.

Other ADAMs have been considered for treating angioplasty, acute coronary syndrome, prevention of restenosis on stents, and prevention of excess adhesion following surgical procedures, prevention of metastasis, as well as for degradation of specific proteins, such as, for example, amyloid precursor protein.

Polynucleotides:

The highly conserved amino acids in the disintegrin domain of zdint1 can be used as a tool to identify new family members. For instance, reverse transcription-polymerase chain reaction (RT-PCR) can be used to amplify sequences encoding the conserved disintegrin domain from RNA obtained from a variety of tissue sources or cell lines. In particular, highly degenerate primers designed from the zdint1 sequences are useful for this purpose.

The present invention also provides polynucleotide molecules, including DNA and RNA molecules, that encode the zdint1 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zdint1 polypeptide of SEQ ID NO:2. Those skilled in the art will recognize that the degenerate sequence of SEQ ID NO:3 also provides all RNA sequences encoding SEQ ID NO:2 by substituting U for T. Thus, zdint1 polypeptide-encoding polynucleotides comprising nucleotide 1 to nucleotide 2088 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A \| G | Y | C \| T |
| Y | C \| T | R | A \| G |
| M | A \| C | K | G \| T |
| K | G \| T | M | A \| C |
| S | C \| G | S | C \| G |
| W | A \| T | W | A \| T |
| H | A \| C \| T | D | A \| G \| T |
| B | C \| G \| T | V | A \| C \| G |
| V | A \| C \| G | B | C \| G \| T |
| D | A \| G \| T | H | A \| C \| T |
| N | A \| C \| G \| T | N | A \| C \| G \| T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn \| Asp | B |  | RAY |
| Glu \| Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene*

18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

The isolated polynucleotides of the present invention include DNA and RNA. Methods for preparing DNA and RNA are well known in the art. In general, RNA is isolated from a tissue or cell that produces large amounts of zdint1 RNA. Such tissues and cells are identified by Northern blotting (Thomas, *Proc. Natl. Acad. Sci. USA* 77:5201, 1980), and include heart, brain, skeletal muscle, spinal cord, fetal heart, and fetal brain. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding zdint1 polypeptides are then identified and isolated by, for example, hybridization or PCR.

A full-length clone encoding zdint1 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zdint1 or other specific binding partners.

Zdint1 polynucleotide sequences disclosed herein can also be used as probes or primers to clone 5' non-coding regions of a zdint1 gene. In view of the tissue-specific expression observed for zdint1 by Northern blotting, this gene region is expected to provide for heart-, brain-, spinal cord-, and skeletal muscle-specific expression. Promoter elements from a zdint1 gene could thus be used to direct the tissue-specific expression of heterologous genes in, for example, transgenic animals or patients treated with gene therapy. Cloning of 5' flanking sequences also facilitates production of zdint1 proteins by "gene activation" as disclosed in U.S. Pat. No. 5,641,670. Briefly, expression of an endogenous zdint1 gene in a cell is altered by introducing into the zdint1 locus a DNA construct comprising at least a targeting sequence, a regulatory sequence, an exon, and an unpaired splice donor site. The targeting sequence is a zdint1 5' non-coding sequence that permits homologous recombination of the construct with the endogenous zdint1 locus, whereby the sequences within the construct become operably linked with the endogenous zdint1 coding sequence. In this way, an endogenous zdint1 promoter can be replaced or supplemented with other regulatory sequences to provide enhanced, tissue-specific, or otherwise regulated expression.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323–356 (1984) and Climie et al., *Proc. Natl. Acad. Sci. USA* 87:633–637 (1990).

The present invention further provides counterpart polypeptides and polynucleotides from other species (orthologs). These species include, but are not limited to mammalian, avian, amphibian, reptile, fish, insect and other vertebrate and invertebrate species. Of particular interest are zdint1 polypeptides from other mammalian species, including murine, porcine, ovine, bovine, canine, feline, equine, and other primate polypeptides. Orthologs of human zdint1 can be cloned using information and compositions provided by the present invention in combination with conventional cloning techniques. For example, a cDNA can be cloned using mRNA obtained from a tissue or cell type that expresses zdint1 as disclosed herein. Such tissue or cell type would include, for example, heart, brain, spinal cord, and skeletal muscle. Suitable sources of mRNA can be identified by probing Northern blots with probes designed from the sequences disclosed herein. A library is then prepared from mRNA of a positive tissue or cell line. A zdint1-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zdint1 sequence disclosed herein. Within an additional method, the cDNA library can be used to transform or transfect host cells, and expression of the cDNA of interest can be detected with an antibody to zdint1 polypeptide. Similar techniques can also be applied to the isolation of genomic clones.

Those skilled in the art will recognize that the sequence disclosed in SEQ ID NO:1 represents a single allele of human zdint1 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zdint1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zdint1 polypeptides that are substantially homologous to the polypeptides of SEQ ID NO:2 and their orthologs. The term "substantially homologous" is used herein to denote polypeptides having about 50%, preferably 60% more preferably at least 70%, and even more preferably 80% sequence identity to the sequences shown in SEQ ID NO:2 or their orthologs. Such polypeptides will more preferably be at least 90% identical, and most preferably 95% or more identical to SEQ ID NO:2 or its orthologs.) Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes) The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zdint1. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The present invention includes nucleic acid molecules that encode a polypeptide having one or more conservative amino acid changes, compared with the amino acid sequence of SEQ ID NO:2. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zdint1 polypeptides or substantially homologous zdint1 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. The present invention thus includes polypeptides of from 383 to 464 amino acid residues that comprise a sequence that is at least 50%, preferably at least 60%, and more preferably 80% or more identical to the corresponding region of SEQ ID NO:2. Polypeptides comprising affinity tags can further comprise a proteolytic cleavage site between the zdint1 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 4-continued

| Conservative amino acid substitutions | |
|---|---|
| Small: | glycine |
| | alanine |
| | serine |
| | threonine |
| | methionine |

The present invention further provides a variety of polypeptide fusions and related multimeric proteins comprising one or more polypeptide fusions. For example, a disintegrin polypeptide domain can be prepared as a fusion to a dimerizing protein, as disclosed in U.S. Pat. Nos. 5,155,027 and 5,567,584. Preferred dimerizing proteins in this regard include other disintegrin polypeptide domains or disintegrin polypeptide domain fragments. Disintegrin polypeptide domain fusions, or disintegrin polypeptide domain fragment fusions, can be expressed in genetically engineered cells to produce a variety of multimeric disintegrin-like analogs. Auxiliary domain polypeptides can be fused to disintegrin domain polypeptides to target them to specific cells, tissues, or macromolecules (e.g., heart, brain, spinal cord, skeletal muscle, platelets). For example, a protease polypeptide domain, or protease polypeptide fragment or protein, could be targeted to a predetermined cell type by fusing it to a disintegrin polypeptide domain or fragment that specifically binds to an integrin polypeptide or integrin-like polypeptide on the surface of the target cell. In this way, polypeptides, polypeptide fragments and proteins can be targeted for therapeutic or diagnostic purposes. Such disintegrins or protease polypeptide domains or fragments can be fused to two or more moieties, such as an affinity tag for purification and a targeting-disintegrin domain. Polypeptide fusions can also comprise one or more cleavage sites, particularly between domains. See Tuan et al., *Connective Tissue Research* 34:1–9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of zdint1 polypeptide can be fused to *E. coli* β-galactosidase (1,021 residues; see Casadaban et al., *J. Bacteriol.* 143: 971–980, 1980), a 10-residue spacer, and a 4-residue factor Xa cleavage site. In a second example, residues of zdint1 polypeptide can be fused to maltose binding protein (approximately 370 residues), a 4-residue cleavage site, and a 6-residue polyhistidine tag.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zdint1 amino acid residues.

Essential amino acids in the polypeptides of the present invention can be identified according to procedures known in the art, such as site-directed mutagenesis or alanine-scanning mutagenesis (Cunningham and Wells, *Science* 244:1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of disintegrin-integrin, or protease interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related disintegrin-like molecules.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zdint1 DNA and polypeptide sequences can be generated through DNA shuffling, as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., disintegrin-cell surface binding or protease activity) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or that retain the disintegrin and or protease activity of the wild-type zdint1 protein. Such polypeptides may include additional amino acids from, for example, a secretory domain, a propeptide domain, a protease domain, part or all of a transmembrane and intracellular domains, including amino acids responsible for intracellular signaling; a fusion domains; affinity tags; and the like.

For any zdint1 polypeptide, including variants and fusion proteins, one of ordinary skill in the art can readily generate a fully degenerate polynucleotide sequence encoding that variant using the information set forth in Tables 1 and 2 above.

Protein Production

The zdint1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zdint1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zdint1 polypeptide into the secretory pathway of a host cell, a secretory signal sequence (also known as a leader sequence, prepro sequence or pre sequence) is provided in the expression vector. The secretory signal sequence may be derived from another secreted protein (e.g., t-PA) or synthesized de novo. The secretory signal sequence is operably linked to the zdint1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830). Polypeptides and peptide fragments of the present invention are considered biologically active in the absence of the native signal sequence.

The protease domain of zdint1 can be substituted by a heterologous sequence providing a different protease domain. In this case, the fusion product can be secreted, and the disintegrin domain of zdint1 can direct the protease domain to a specific tissue described above. This substituted protease domain can be chosen from the protease domains represented by the DP protein families, or domains from other known proteases.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Bangalore*) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zdint1 baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zdint1 polypeptide into a baculovirus genome maintained in *E. coli* as a large plasmid called a "bacmid." See, Hill-Perkins, M. S. and Possee, R. D., *J Gen Virol* 71:971–6, 1990; Bonning, B. C. et al., *J Gen Virol* 75:1551–6, 1994; and, Chazenbalk, G. D., and Rapoport, B., *J Biol Chem* 270:1543–9, 1995. In addition, transfer vectors can include an in-frame fusion with DNA encoding an epitope tag at the C- or N-terminus of the expressed zdint1 polypeptide, for example, a Glu-Glu epitope tag (Grussenmeyer, T. et al., *Proc. Natl. Acad. Sci.* 82:7952–4, 1985). Using a technique known in the art, a transfer vector containing zdint1 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zdint1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2–5 \times 10^5$ cells to a density of $1–2 \times 10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the zdint1 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., ibid.). When expressing a zdint1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Protein Isolation

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zdint1 polypeptides (or chimeric zdint1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by a combination of procedures including, but not limited to, anion and cation exchange chromatography, size exclusion, and affinity chromatography. See Example 3 for a procedure. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

Fragments/Fusion Proteins

To direct the export of a zdint1 polypeptide from the host cell, the zdint1 DNA is linked to a second DNA segment encoding a secretory peptide, such as a t-PA secretory peptide. To facilitate purification of the secreted receptor polypeptide, a C-terminal extension, such as a poly-histidine tag, substance P, Flag peptide (Hopp et al., *Bio/Technology* 6:1204–1210, 1988; available from Eastman Kodak Co., New Haven, Conn.) or another polypeptide or protein for which an antibody or other specific binding agent is available, can be fused to the zdint1 polypeptide.

Moreover, using methods described in the art, polypeptide fusions, or hybrid zdint1 proteins, are constructed using regions or domains of the inventive zdint1 in combination with those of other disintegrin-like molecules. (e.g. ADAM, MDC, and SVMP), or heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domains conferring a biological function may be swapped between zdint1 of the present invention with the functionally equivalent domains from another family member, such as ADAM, MDC, and SVMP. Such domains include, but are not limited to, conserved motifs such as the secretory signal sequence, protease, RGD, cysteine, and disintegrin domains. Such fusion proteins would be expected to have a biological functional profile that is the same or similar to polypeptides of the present invention or other known disintegrin-like family proteins (e.g. ADAMs, MDCs, and SVMPs), depending on the fusion constructed. Moreover, such fusion proteins may exhibit other properties as disclosed herein.

zdint1 polypeptides or fragments thereof may also be prepared through chemical synthesis. zdint1 polypeptides may be monomers or multimers; glycosylated or non-glycosylated; pegylated or non-pegylated; and may or may not include an initial methionine amino acid residue.

Chemical Synthesis of Polypeptides

Zdint1 polypeptides, peptides, variants and or fragments thereof may also be prepared through chemical synthesis. TML polypeptides may be monomers or multimers; glycosylated or non-glycosylated; pegylated or non-pegylated; amidated or non-amidated; sulfated or non-sulfated; and may or may not include an initial methionine amino acid residue. For example, TML polypeptides can also be synthesized by exclusive solid phase synthesis, partial solid phase methods, fragment condensation or classical solution synthesis. The polypeptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluoro-phosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595, 1970.

After the entire assembly of the desired peptide, the peptide-resin is cleaved with a reagent with proper scavengers. The Fmoc peptides are usually cleaved and deprotected by TFA with scavengers (e.g., H2O, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury (II) acetate and alternatively by iodine, thallium(III)trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The disintegrin loop (residue 438 to residue 449 of SEQ ID NO:2) is of particular interest for use in assays and treatment of disorders of the heart, brain, spinal cord, and skeletal muscle. For these purposes the disintegrin loop peptide synthesized includes the terminal cysteine residues and thus, would be from residue 437 to residue 450 of SEQ ID NO:2. This peptide can be synthesized as a linear peptide or a disulfide linked peptide. Peptides having disulfide bonds between residues can be 438, 444, and 450 are of particular interest. See Jia, L. G., ibid for additional description of peptide synthesis and disulfide linkage.

One skilled in the art will recognize that it is useful to design and synthesize new binding peptides using the integrin binding peptides of zdint1 as a model. Methods for synthesizing such peptides are described by P. L. Barker et al., *J. Med. Chem.* 35: 2040–2048, 1992, and L. Jia et al., *J. Biol. Chem.* 272: 13094–13102, 1997. As the structural conformation of the integrin binding peptide is critical, it is recognized that although some amino acid substitutions will not change the conformation of the peptides, the cyclization of the peptide is advantageously conserved. Synthetic peptides are useful as agonists or antagonsits for zdint1 and could be assayed.

Assays

The activity of zdint1 polypeptides can be measured using a variety of assays that measure, for example, cell-cell interactions, proteolysis, extracellular matrix formation or remodeling. Additionally, other biological functions associated with disintegrin family members or with integrin/disintegrin interactions, apoptosis, proliferation or differentiation can also be measured. Of particular interest is a change in platelet aggregation. Assays measuring platelet aggregation are well known in the art. For a general reference, see Dennis, *Proc. Natl. Acad. Sci.* 87: 2471–2475, 1989.

Another assay of interest measures or detects changes in differentiation, development and/or and electrical coupling of muscle cells or myocytes. Additionally, the effects of a zdint1 polypeptides on cell-cell interactions of fibroblasts, myoblasts, nerve cells, white blood cells, endothelial cells and tumor cells would be of interest to measure. Yet another assays examines changes in protease activity and apoptosis.

The activity of molecules of the present invention can be measured using a variety of assays that, for example, measure neogenesis or hyperplasia (i.e., proliferation) of cardiac cells based on the tissue specificity in adult heart. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured using cultured cardiac cells or in vivo by administering molecules of the claimed invention to an appropriate animal model. Generally, proliferative effects are observed as an increase in cell number and therefore, may include inhibition of apoptosis, as well as mitogenesis. Cultured cells include cardiac fibroblasts, cardiac myocytes, skeletal myocytes, human umbilical vein endothelial cells from primary cultures. Established cell lines include: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992) and LNCap.FGC adenocarcinoma cells (ATCC No. CRL-1740). Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabelled nucleotides (Cook et al., *Analytical Biochem.* 179: 1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. The novel polypeptides of the present invention are useful for studies to isolate mesenchymal stem cells and cardiac myocyte progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, zdint1 polypeptides may stimulate inhibition or proliferation of myocytes, smooth muscle cells, osteoblasts, adipocytes, chrondrocytes and endothelial cells. Molecules of the present invention may, while stimulating proliferation or differentiation of cardiac myocytes, inhibit proliferation or differentiation of adipocytes, by virtue of their effect on common precursor/stem cells. Thus, molecules of the present invention have use in inhibiting chondrosarcomas, atherosclerosis, restenosis and obesity.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses,* 161–171, 1989; all incorporated herein by reference).

In vivo assays for evaluating cardiac neogenesis or hyperplasia include treating neonatal and mature rats with the molecules of the present invention. The animals' cardiac function is measured as heart rate, blood pressure, and cardiac output to determine left ventricular function. Postmortem methods for assessing cardiac improvement include: increased cardiac weight, nuclei/cytoplasmic volume, staining of cardiac histology sections to determine proliferating cell nuclear antigen (PCNA) vs. cytoplasmic actin levels (Quaini et al., *Circulation Res.* 75:1050–1063, 1994 and Reiss et al., *Proc. Natl. Acad. Sci.* 93:8630–8635, 1996.)

Assays measuring in vivo effects of synthetic zdint1 agonists include a Left Ventricular Hypertrophy model (A. M. Feldman et al., *Circ. Res.* 73: 184–192, 1993), which measures remodeling and repair after congestive heart failure and chronic pressure overload.

Proteins, including alternatively spliced peptides, of the present invention are useful for tumor suppression, and growth and differentiation either working in isolation, or in conjunction with other molecules (growth factors, cytokines, etc.) in brain, heart, spinal column, and skeletal muscle cells. Alternative splicing of zdint1 may be cell-type specific and confer activity to specific tissues.

Proteins of the present invention are useful for delivery of therapeutic agents such as, but not limited to, proteases, radionuclides, chemotherapy agents, and small molecules. Effects of these therapeutic agents can be measured in vitro using cultured cells or in vivo by administering molecules of the claimed invention to the appropriate animal model. For instance, zdint1 transfected expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached) A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

Within yet another embodiment is provided an oligonucleotide probe or primer comprising at least 14 contiguous nucleotides of a polynucleotide of SEQ ID NO:1 or a sequence complementary to SEQ ID NO:1.

Agonists and Antagonists

In view of the tissue distribution (heart, brain, spinal cord and skeletal muscle) observed for zdint1 expression, agonists (including the native disintegrin and protease domains) and antagonists have enormous potential in both in vitro and in vivo applications. Compounds identified as zdint1 agonists and antagonists are useful for studying cell-cell interactions, myogenesis, apoptosis, neurogenesis, connective tissue disorders, chondrogenesis, arthritis, tumor proliferation and suppression, extracellular matrix proteins, repair and remodeling of ischemia reperfusion and inflammation in vitro and in vivo. For example, zdint1 and agonist compounds are useful as components of defined cell culture media, and may be used alone or in combination with other cytokines and hormones to replace serum that is commonly used in cell culture. Agonists are thus useful in specifically promoting the growth and/or development of cells of the myeloid lineages in culture. Additionally, zdint1 polypeptides and zdint1 agonists, including small molecules are useful as a research reagent, such as for the expansion, differentiation, and/or cell-cell interactions of heart, brain, spinal cord, or skeletal muscle cells. zdint1 polypeptides are added to tissue culture media for these cell types.

Antagonists

Antagonists are also useful as research reagents for characterizing sites of complementary/anti-complementary interaction. Inhibitors of zdint1 activity (zdint1 antagonists) include anti-zdint1 antibodies and soluble zdint1 receptors, as well as other peptidic and non-peptidic agents (including ribozymes).

zdint1 can also be used to identify inhibitors (antagonists) of its activity. Test compounds are added to the assays disclosed herein to identify compounds that inhibit the activity of zdint1. In addition to those assays disclosed herein, samples can be tested for inhibition of zdint1 activity within a variety of assays designed to measure disintegrin/integrin binding or the stimulation/inhibition of zdint1-dependent cellular responses. For example, zdint1-responsive cell lines can be transfected with a reporter gene construct that is responsive to a zdint1-stimulated cellular pathway. Reporter gene constructs of this type are known in the art, and will generally comprise a DNA response element operably linked to a gene encoding an assayable protein, such as luciferase, or a metabolite. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8): 1087–94; 1990. Hormone response elements are reviewed in Beato, *Cell* 56:335–44; 1989. The most likely reporter gene construct would contain a disintegrin that, upon binding an integrin, would signal intracellularly through, for example, a SRE reporter. Candidate compounds, solutions, mixtures or extracts are tested for the ability to inhibit the activity of zdint1 on the target cells, as evidenced by a decrease in zdint1 stimulation of reporter gene expression. Assays of this type will detect compounds that directly block zdint1 binding to cell-surface receptors, i.e., integrin or the anti-complementary member of a complementary/anti-complementary pair, as well as compounds that block processes in the cellular pathway subsequent to complement/anti-complement binding. In the alternative, compounds or other samples can be tested for direct blocking of zdint1 binding to an integrin using zdint1 tagged with a detectable label (e.g., $^{125}$I, biotin, horseradish peroxidase, FITC, and the like). Within assays of this type, the ability of a test sample to inhibit the binding of labeled zdint1 to the integrin is indicative of inhibitory activity, which can be confirmed through secondary assays. Integrins used within binding assays may be cellular integrins or isolated, immobilized integrins.

An amino acid sequence comprising the "ECD" integrin binding component of zdint1, (residues 443 to 445 of SEQ ID NO: 2), which is analogous to the "RGD", integrin binding loop, may also be used as an inhibitor. Such an inhibitor would bind an integrin other than its naturally occurring integrin by nature of its folding structure. A particular interest in such an inhibitor would be to mediate platelet aggregation. Assays measuring binding and inhibition as well as platelet aggregation are known in the art.

A zdint1 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to evaluate effects and potential of dimerization of zdint1 with itself or other disintegrin family members. Such fusions would also be useful to isolate the corresponding integrin(s) that zdint1 binds. For use in assays, the chimeras are bound to a support via the $F_c$ region and used in an ELISA format.

A zdint1 integrin-binding polypeptide can also be used for purification of integrin. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing integrins are passed through the column one or more times to allow integrins to bind to the integrin binding loop polypeptide. The integrin is then eluted using changes in salt concentration, chaotropic agents (guanidine HCl), or pH to disrupt integrin-receptor binding.

An assay system that uses a ligand-binding receptor (or an antibody, one member of a complementary/anti-complementary pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complementary/anti-complementary pair is present in the sample, it will bind to the immobilized receptor, antibody or member, respectively, causing a change in the refractive index of the medium, which is detected as a change in surface plasmon resonance of the gold film. This system allows the determination of on-and off-rates, from which binding affinity can be calculated, and assessment of stoichiometry of binding.

Another method to assay cell-cell interactions caused by zint1 polypeptides, peptides, or variants is with a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zdint1 polypeptide, peptide, variant, agonists, or antagonists. Preferably, the microphysiometer is used to measure responses of a zdint1-responsive eukaryotic cell, compared to a control eukaryotic cell that does not respond to zdint1 polypeptide, peptide, or variant. Zdint1-responsive eukaryotic cells comprise cells into which a receptor for zdint1 has been transfected creating a cell that is responsive to zdint1 polypeptide, peptide, or variant; or cells naturally responsive to zdint1 such as, for example, cells derived from the kidney or small intestine. Differences, measured by a change, for example, an increase or diminution in extracellular acidification, in the response of cells exposed to zdint1 polypeptide, peptide, or variant relative to a control not exposed to zdint1 polypeptide, peptide, or variant, are a direct measurement of zdint1-modulated cellular responses. Moreover, such zdint1-modulated responses can be assayed under a variety of stimuli. Using the microphysiometer, there is provided a method of identifying agonists of zdint1 polypeptide, comprising providing cells responsive to a zdint1 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Moreover, culturing a third portion of the cells in the presence of zdint1 polypeptide and the absence of a test compound can be used as a positive control for the zdint1-responsive cells, and as a control to compare the agonist activity of a test compound with that of the zdint1 polypeptide. Moreover, using the microphysiometer, there is provided a method of identifying antagonists of zdint1 polypeptide, comprising providing cells responsive to a zdint1 polypeptide, culturing a first portion of the cells in the presence of zdint1 and the absence of a test compound, culturing a second portion of the cells in the presence of zdint1 and the presence of a test compound, and detecting a change, for example, an increase or a diminution in a cellular response of the second portion of the cells as compared to the first portion of the cells. The change in cellular response is shown as a measurable change in extracellular acidification rate. Antagonists and agonists, for zdint1 polypeptide, can be rapidly identified using this method.

Moreover, polypeptides, peptides and variants of zdint1 can be used to identify cells, tissues, or cell lines which respond to a zdint1-stimulated pathway. The microphysiometer, described above, can be used to rapidly identify ligand-responsive cells, such as cells responsive to zdint1 polypeptides peptides and variants of the present invention. Cells can be cultured in the presence or absence of zdint1 polypeptides, peptides and variants. Those cells which elicit a measurable change in extracellular acidification in the presence of zdint1 polypeptides, peptides and variants are responsive to zdint1. Such cell lines, can be used to identify antagonists and agonists of zdint1 polypeptide as described above.

Integrin polypeptides and other receptor polypeptides which bind disintegrin polypeptides, and variants thereof, can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

Soluble forms of zdint1 polypeptides may act as antagonsits to zdint1 polypeptides, and would be useful to modulate the effects of zdint1 in heart, brain, skeletal muscle and spinal cord. Additionally, soluble zdint1 peptides and fragments can disrupt the integrin-mediated attachment of a cell to the extracellular matrix.

Antibodies:

zdint1 polypeptides can also be used to prepare antibodies that specifically bind to zdint1 epitopes, peptides or polypeptides. The zdint1 polypeptide or a fragment thereof serves as an antigen (immunogen) to inoculate an animal and elicit an immune response. Suitable antigens would include fragments of the zdint1 polypeptide encoded by SEQ ID NO:2 which represent six or more contiguous hydrophilic amino acids. Such antigenic regions would be, for example, from amino acid residue 159 to 164 (SEQ ID NO:7); amino acid residue 158 to 163 (SEQ ID NO:8); amino acid residue 518 to 523 (SEQ ID NO:9); amino acid residue 658 to 663 (SEQ ID NO:10); and amino acid residue 190 to 195 (SEQ ID NO:11). Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zdint1 polypeptide or a fragment thereof. The immunogenicity of a zdint1 polypeptide may be increased through the use of an adjuvant, such as alum (aluminum hydroxide) or Freund's complete or incomplete adjuvant. Polypeptides useful for immunization also include fusion polypeptides, such as fusions of zdint1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to zdint1 protein or peptide, and selection of antibody display libraries in phage or similar vectors (for instance, through use of immobilized or labeled zdint1 protein or peptide). Genes encoding polypeptides having potential zdint1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zdint1 sequences disclosed herein to identify proteins which bind to zdint1. These "binding proteins" which interact with zdint1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zdint1 "antagonists" to block zdint1 binding and signal transduction in vitro and in vivo. These anti-zdint1 binding proteins would be useful for inhibiting, for example, platelet aggregation, apoptosis, neurogenesis, myogenesis, tumor formation, and cell-cell interactions in general.

Antibodies are determined to be specifically binding if: 1) they exhibit a threshold level of binding activity, and/or 2) they do not significantly cross-react with related polypeptide molecules. First, antibodies herein specifically bind if they bind to a zdint1 polypeptide, peptide or epitope with a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect zdint1 but not known related polypeptides using a standard Western blot analysis (Ausubel et al., ibid.). Examples of known related polypeptides are orthologs, proteins from the same species that are members of a protein family, zdint1 polypeptides, and non-human zdint1. Moreover, antibodies may be "screened against" known related polypeptides to isolate a population that specifically binds to the inventive polypeptides. For example, antibodies raised to zdint1 are adsorbed to related polypeptides adhered to insoluble matrix; antibodies specific to zdint1 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984.

A variety of assays known to those skilled in the art can be utilized to detect antibodies which specifically bind to zdint1 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zdint1 protein or polypeptide.

Antibodies to zdint1 may be used for tagging cells that express zdint1; for isolating zdint1 by affinity purification; for diagnostic assays for determining circulating levels of zdint1 polypeptides; for detecting or quantitating soluble zdint1 as marker of underlying pathology or disease; in analytical methods employing FACS; for screening expression libraries; for generating anti-idiotypic antibodies; and as neutralizing antibodies or as antagonists to block zdint1 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zdint1 or fragments thereof may be used in vitro to detect denatured zdint1 or fragments thereof in assays, for example, Western Blots or other assays known in the art.

The present invention also provides polypeptide fragments or peptides comprising an epitope-bearing portion of a zacrp2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat. Acad. Sci. USA* 81:3998, 1983).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219: 660, 1983). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting a zacrp2 polypeptide, or by chemical peptide synthesis, as described herein. Moreover, epitopes can be selected by phage display of random peptide libraries (see, for example, Lane and Stephen, *Curr. Opin. Immunol.* 5:268, 1993, and Cortese et al., *Curr. Opin. Biotechnol.* 7:616, 1996). Standard methods for identifying epitopes and producing antibodies from small peptides that comprise an epitope are described, for example, by Mole, "Epitope Mapping," in Methods in Molecular Biology, Vol. 10, Manson (ed.), pages 105–16 (The Humana Press, Inc. 1992), Price, "Production and Characterization of Synthetic Peptide-Derived Antibodies," in *Monoclonal Antibodies:* Production, Engineering, and Clinical Application, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997). Polypeptides, or fragments thereof, of the present invention comprising sequences of amino acids from, for example, SEQ ID NO:7, SEQ ID NO:8, SEQ ID NO:8, SEQ ID NO:10, or SEQ ID NO:11 are epitope bearing.

Bioactive conjugates:

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (integrin or antigen, respectively, for instance). More specifically, zdint1 polypeptides or anti-zdint1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas exotoxin*, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anti-complementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zdint1-cytokine fusion proteins or antibody-cytokine fusion proteins can be used for enhancing in vivo killing of target tissues (for example, brain, heart, spinal cord and skeletal muscle malignancies), if the zdint1 polypeptide or anti-zdint1 antibody targets hyperproliferative brain, heart, spinal cord, or skeletal muscle cells. (See, generally, Hornick et al., *Blood* 89:4437–47, 1997). They described fusion proteins that enable targeting of a cytokine to a desired site of action, thereby providing an elevated local concentration of cytokine. Suitable zdint1 polypeptides or anti-zdint1 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the zdint1 polypeptide or anti-zdint1 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Uses of Polynucleotide/Polypeptide:

Molecules of the present invention can be used to identify and isolate receptors and integrins involved in cell-cell interactions. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Polypeptides and peptides which bind to the zdint1 polypeptides, peptides, and variants fo the present invention can then be eluted and characterized using methods known in the art. Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The molecules of the present invention will be useful in repair and remodeling after an ischemic event, and/or inhibiting platelet aggregation. The polypeptides, nucleic acid and/or antibodies of the present invention can be used in treatment of disorders associated with infarct in brain or heart tissue, and/or platelet aggregation. The molecules of the present invention can be used to modulate proteolysis, apoptosis, neurogenesis, myogenesis, connective tissue disorders, arthritis, chondrogenesis, cell adhesion, cell fusion, and signaling or to treat or prevent development of pathological conditions in such diverse tissue as heart, brain, spinal cord and skeletal muscle. In particular, certain diseases may be amenable to such diagnosis, treatment or prevention. The molecules of the present invention can be used to modulate inhibition and proliferation of neurons and myocytes in heart, brain, spinal cord and skeletal muscle tissues. Disorders which may be amenable to diagnosis, treatment or prevention with zdint1 polypeptides include, for example, Alzheimers's Disease, tumor formation, Multiple Sclerosis, Congestive Heart Failure, Ischemic Reperfusion or infarct, and degenerative diseases.

The zdint1 molecules of the present invention may be particularly useful in the treatment of intimal hyperplasia or restenosis due to acute vascular injury. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, atherectomy, vascular graft emplacement or the like are employed. Hyperplasia may also occur as a delayed response in response to, e.g., graft emplacement or organ transplantation. The dose of zdint1 in the treatment for restenosis will vary with each patient but will generally be in the range of those suggested above.

Advances in the treatment of coronary vascular disease include the use of mechanical interventions to either remove or displace offending plaque material in order to re-establish adequate blood flow through the coronary arteries. Despite the use of multiple forms of mechanical interventions, including balloon angioplasty, reduction atherectomy, placement of vascular stents, laser therapy, or rotoblator, the effectiveness of these techniques remains limited by an approximately 40% restenosis rate within 6 months after treatment.

Restenosis is thought to result from a complex interaction of biological processes including platelet deposition and thrombus formation, release of chemotactic and mitogenic factors, and the migration and proliferation of vascular smooth muscle cells into the intima of the dilated arterial segment.

The inhibition of platelet accumulation at sites of mechanical injury can limit the rate of restenosis in human subjects. Therapeutic use of a monoclonal antibody to platelet GpIIb/IIIa is able to limit the level of restenosis in human subjects (Califf et al., *N. Engl. J. Med.,* 330: 956–961 (1994)). The antibody is able to bind to the GpIIb/IIIa receptor on the surfaces of platelets and thereby inhibit platelet accumulation. This data suggests that inhibition of platelet accumulation at the site of mechanical injury in human coronary arteries is beneficial for the ultimate healing response that occurs.

Gene Therapy:

Polynucleotides encoding zdint1 polypeptides are useful within gene therapy applications where it is desired to increase or inhibit zdint1 activity. If a mammal has a mutated or absent zdint1 gene, the zdint1 gene can be introduced into the cells of the mammal. In one embodiment, a gene encoding a zdint1 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zdint1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zdint1 gene transcription, such as to inhibit cell proliferation in vivo. Polynucleotides that are complementary to a segment of a zdint1-encoding polynucleotide (e.g., a polynucleotide as set froth in SEQ ID NO:1) are designed to bind to zdint1-encoding mRNA and to inhibit translation of such mRNA. Such antisense polynucleotides are used to inhibit expression of zdint1 polypeptide-encoding genes in cell culture or in a subject.

The present invention also provides reagents which will find use in diagnostic applications. For example, the zdint1 gene, a probe comprising zdint1 DNA or RNA or a subsequence thereof can be used to determine if the zdint1 gene is present on chromosome 2q33 or if a mutation has occurred. Detectable chromosomal aberrations at the zdint1 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

Transgenic mice, engineered to express the zdint1 gene, or fragments thereof, and mice that exhibit a complete absence of zdint1 gene function, referred to as "knockout mice" (Snouwaert et al., *Science* 257:1083, 1992), can also be generated (Lowell et al., *Nature* 366:740–42, 1993) by one skilled in the art. These mice can be employed to study the zdint1 gene, gene fragments, and the protein encoded thereby in an in vivo system.

Chromosomal Localization:

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md.), and can be searched with a gene sequence of interest for the mapping data contained within these short genomic landmark STS sequences.

For pharmaceutical use, the proteins of the present invention can be administered orally, rectally, parenterally, intracisternally, intravaginally, intraperitoneally, topically (as powders, ointments, drops or transdermal patch) bucally, or as a pulmonary or nasal inhalant. Intravenous administration will be by bolus injection or infusion over a typical period of one to several hours. In general, pharmaceutical formulations will include a zdint1 protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zdint1 is an amount sufficient to produce a clinically significant change in extracellular matrix remodeling, scar tissue formation, tumor suppression, platelet aggregation, apoptosis, myogenesis, neurogenesis, electrical coupling, blood flow and/or cell proliferation in brain, heart, spinal cord, and skeletal muscle.

The invention is further illustrated by the following non-limiting examples.

EXAMPLES

Example 1

Extension of EST Sequence

The novel zdint1 polypeptide-encoding polynucleotides of the present invention were initially identified by querying an EST database. This query identified an expressed sequence tag (EST) to nucleotide 1097 to nucleotide 1415 of SEQ ID NO: 1. A cDNA clone, corresponding to this EST was obtained and the deduced amino acid sequence was determined to be incomplete. Primers ZC17,991 (SEQ ID NO:4) and ZC17,992 (SEQ ID NO:5) were used to screen an arrayed fetal brain cDNA plasmid library to identify clones of zdint1. Thermocycler conditions were as follows: one cycle at 94° C. for 1 minute 30 seconds; followed by thirty cycles at 94° C. for 10 seconds, 64° C. for 20 seconds, 72° C. for 30 seconds, followed by one cycle at 72° C. for 5 minutes, followed by a 4° C. hold. A sample of the reaction contents was electrophoresed on a 4% agarose gel to identify positive pools. These pools were screened by polymerase chain reaction with ZC17,992 (SEQ ID NO:5) and the vector primer ZC13,006 (SEQ ID NO:6). Thermocycler conditions were as follows: one cycle at 94° C. for 1 minute 30 seconds; followed by five cycles at 94° C. for 10 seconds, 68° C. for 2 minutes, followed by twenty-five cycles at 94° C. for 10 seconds, 62° C. for 20 seconds, 72° C. for 2 minutes, followed by one cycle at 72° C. for 10 minutes, followed by a 4° C. hold. A sample of the reaction contents was electrophoresed on a 1% agarose gel and a band of ~1.5 kb was further electrophoresed on a 1% preparative gel and the resulting band gel purified using commercially available gel purification reagents and protocol (QIAEX II Gel Extraction Kit; Qiagen, Inc., Santa Clarita, Calif.). This fragment was sequenced and was determined to extend the amino acid sequence of zdint1 in the 5' direction.

Example 2

Tissue Distribution

Analysis of tissue distribution was performed by the Northern blotting technique using Human Multiple Tissue and Master Dot Blots from Clontech (Palo Alto, Calif.), and a human vascular tissue blot prepared in-house. The human vascular blot was prepared from the following cell lines: Human Umbilical Vein Endothelial Cells (Cascade Biologics, Inc., Portland, Oreg.), Human Pulmonary Artery Endothelial Cells (Cascade Biologics, Inc., Portland, Oreg.), Human Aortic Endothelail Cells, (Cascade Biologics, Inc., Portland, Oreg.), Aortic Smooth Muscle Cells (Clonetics, San Diego, Calif.), Human Intestinal Smooth Muscle Cells (American Type Culture Collectio, Manasas, Va.), Normal Human Lung Fibroblast, Clonetics, San Diego, Calif.) and Normal Human Dermal Fibroblast-Neonatal, Clonetics, San Diego, Calif.). Messenger RNA was extracted and blots prepared by methods known in the art. The probe was obtained by restriction digest of the original cDNA clone with a restriction endonuclease, PstI. The reaction mixture was electrophoresed on a preparative agarose gel and two bands, corresponding to a 239 base pair fragment and a 223 base pair fragment from the cDNA clone, were gel purified using commercially available gel purification reagents and protocol from Qiagen, Inc. A probe was made by pooling the purified DNA from both bands and was random prime labeled with $^{32}$P using a commercially available kit (Rediprime DNA labeling system; Amersham Corp., Arlington Heights, Ill.). The probe was then purified using a NUC-TRAP push column (Stratagene Cloning Systems, La Jolla, Calif.). EXPRESSHYB (Clontech) solution was used for pre-hybridization and hybridization. The hybridization solution consisted of 8 ml EXPRESSHYB, 80 µl Sheared Salmon Sperm DNA (10 mg/ml, 5 Prime-3 Prime, Boulder, Colo.), 48 µl Human Cot-1 DNA (1 mg/ml, Gibco BRL), and 57 µl labeled probe ($2.3 \times 10^{-5}$ CPM/µl). Hybridization took place overnight at 50° C., and the blots were then washed in 2×SSC and 0.1% SDS at ambient room temperature, then 2×SSC and 0.1% SDS at 60° C., followed by 0.1×SSC and 0.1% SDS at 60° C. The blots were exposed overnight and developed. Strong signals of three transcript sizes, approximately 3.0 kb, 4.4 kb, and 7.5 kb, were observed in heart on the multiple tissue Northern blots. Faint signals of the same transcript sizes were observed in brain and spinal cord. An fainter signal of the three transcript sizes was observed in skeletal muscle. The Master Dot Blot showed strong signals in brain, heart, fetal brain, and fetal heart. For the human vascular blot, a strong signal at 3–3.5 kb in human aortic endothelial cells and weaker signals in aortic smooth muscle cells and normal human lung fibroblast cells was observed.

Example 3

Protein Purification

Purification conditions for zdint1 with N- and C-terminal EE tags:

E. coli, Pichia, CHO and BHK cells are transfected with expression vectors containing the DNA sequence of SEQ ID NO:1, or a portion thereof, operably linked to a polynucleotide encoding a Glu-Glu tag. Zdint1 protein is expressed in conditioned media of E. coli, Pichia methanolica, and or chinese hamster ovary (CHO) and baby hamster kidney (BHK) cells. For zdint1 expressed in E. coli and Pichia, the media is not concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter, as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 50.0 ml sample of anti-EE Sepharose, prepared as described below, is added and the mixture gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.), and the gel is washed with 30 column volumes of phosphate buffered saline (PBS). The unretained flow-through fraction is discarded. Once the absorbance of the effluent at 280 nM is less than 0.05, flow through the column is reduced to zero, and the anti-EE Sepharose gel is washed with 2.0 column volumes of PBS containing 0.2 mg/ml of EE peptide (AnaSpec, San Jose, Calif.). After 1.0 h at 4° C., flow is resumed and the eluted protein collected. This fraction is referred to as the peptide elution. The anti-EE Sepharose gel is then washed with 2.0 column volumes of 0.1 M glycine, pH 2.5, and the glycine wash is collected separately. The pH of the glycine-eluted fraction is adjusted to 7.0 by the addition of a small volume of 10X PBS and stored at 4° C. for future analysis, if needed.

The peptide elution is concentrated to 5.0 ml using a 15,000 molecular weight cutoff membrane concentrator (Millipore, Bedford, Mass.), according to the manufacturer's instructions. The concentrated peptide elution is then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two-ml fractions are collected and the absorbance at 280 nM monitored. The first peak of material absorbing at 280 nM and eluting near the void volume of the column is collected. This fraction is pure zdint1 NEE or zdint1 CEE. The pure material is concentrated as described above, analyzed by SDS-PAGE and Western blotting with anti-EE antibodies, aliquoted, and stored at –80° C. according to standard procedures.

Preparation of Anti-EE Sepharose:

A 100 ml bed volume of protein G-Sepharose (Pharmacia, Piscataway, N.J.) is washed 3 times with 100 ml of PBS containing 0.02% sodium azide using a 500 ml Nalgene 0.45 micron filter unit. The gel is washed with 6.0 volumes of 200 mM triethanolamine, pH 8.2 (TEA, Sigma, St. Louis, Mo.). and an equal volume of EE antibody solution containing 900 mg of antibody is added. After an overnight incubation at 4° C., unbound antibody is removed by washing the resin with 5 volumes of 200 mM TEA as described above. The resin is resuspended in 2 volumes of TEA, transferred to a suitable container, and dimethylpimilimidate-2HCl (Pierce, Rockford, Ill.), dissolved in TEA, is added to a final concentration of 36 mg/ml of gel. The gel is rocked at room temperature for 45 min and the liquid is removed using the filter unit as described above. Nonspecific sites on the gel are then blocked by incubating for 10 min at room temperature with 5 volumes of 20 mM ethanolamine in 200 mM TEA. The gel is then washed with 5 volumes of PBS containing 0.02% sodium azide and stored in this solution at 4° C.

Purification of Untagged Zdint1

E. coli, Pichia, CHO and BHK cells are transfected with expression vectors containing the DNA sequence of SEQ ID NO:1, or a portion thereof. The procedure described below is used for protein expressed in conditioned medium of *E. coli, Pichia methanolica*, and Chinese hamster ovary (CHO) and baby hamster kidney (BHK) cells. For zdint1 expressed in *E. coli* and *Pichia*, however, the medium is not be concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) S10Y3 membrane. The concentrated material is again be sterile-filtered with the Gelman filter as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim).

The procedures outlined below are adaptations of those used to purify metalloprotease/disintegrins from *Crotalus viridus* and *Crotalus atrox* venom (Liu et al., Toxicol. 33: 1289–1298, 1995; Shimokawa et al., Arch Biochem Biophys 343: 35–43, 1997). A combination of procedures including, but not limited to, anion and cation exchange chromatography, size exclusion, and affinity chromatography is used to purify untagged zdint1.

Concentrated conditioned medium is diluted 1/10 in line with 10 mM borate buffer, pH 9.0, 0.1 M NaCl, and 2.0 mM $CaCl_2$ using the BioCad Sprint HPLC (PerSeptive BioSystems, Framingham, Mass.). The material is pumped onto a 3.5×20 cm Poros HQ (PerSeptive BioSystems, Framingham, Mass.) column at 5 ml/min. The column is washed with loading buffer, and when the absorbance of the effluent is less than 0.05, the column is developed with a linear gradient of NaCl from 0.1 M to 1.0 M NaCl. Fractions containing zdint1 are identified by SDS-PAGE and Western blotting with anti-zdint1 peptide antibodies. zdint1-containing fractions are pooled together, and concentrated using an Amicon stirred cell concentrator fitted with a YM-10 membrane. The Poros HQ pool is then chromatographed on a Sephadex G-75 column equilibrated in 10 mM sodium phosphate, pH 7.0. Fractions containing zdint1 are identified and pooled together, as described above, and applied to a 1.0×5 cm Poros HA hydroxyapatite column at 1.0 ml/min using the BioCad Sprint HPLC. The column is washed with loading buffer and developed with a linear gradient from 10 mM to 500 mM sodium phosphate. Fractions contained pure zdint1 are identified by SDS-PAGE and Western blotting, as described above. The purified material is aliquoted and stored as described above.

Example 4

Chromosomal Assignment and Placement of Zdint1

Zdint1 was mapped to chromosome 2 using the commercially available version of the "Stanford G3 Radiation Hybrid Mapping Panel" (Research Genetics, Inc., Huntsville, Ala.). The "Stanford G3 RH Panel" contains PCRable DNAs from each of 83 radiation hybrid clones of the whole human genome, plus two control DNAs (the RM donor and the A3 recipient). A publicly available WWW server allows chromosomal localization of markers.

For the mapping of zdint1 with the "Stanford G3 RH Panel", 20 µl reactions were set up in a PCRable 96-well microtiter plate (Stratagene, La Jolla, Calif.) and used in a "RoboCycler Gradient 96" thermal cycler (Stratagene). Each of the 85 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC20,843 (SEQ ID NO:12), 1 µl antisense primer, ZC20,844 (SEQ ID NO:13), 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and distilled water for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 66° C. and 1 minute and 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of Zdint1 to the framework marker SHGC-56733 with a LOD score of >12 and at a distance of 0 cR_10000 from the marker. The use of surrounding markers positions Zdint1 in the 2q33 region on the integrated LDB chromosome 2 map (The Genetic Location Database, University of Southhampton, WWW server).

Example 5

Synthesis of Peptides

Zdint1-1, a peptide corresponding to amino acid residue 437 (Cys) to amino acid residue 450 (Cys) of SEQ ID NO: 2, is synthesized by solid phase peptide synthesis using a model 431A Peptide Synthesizer (Applied Biosystems/Perkin Elmer, Foster City, Calif.). Fmoc-Glutamine resin (0.63 mmol/g; Advanced Chemtech, Louisville, Ky.) is used as the initial support resin. 1 mmol amino acid cartridges (Anaspec, Inc. San Jose, Calif.) are used for synthesis. A mixture of 2(1-Hbenzotriazol-y-yl 1,1,3,3-tetrahmethylhyluronium hexafluorophosphate (HBTU), 1-hydroxybenzotriazol (HOBt), 2 m N,N-Diisopropylethylamine, N-Methylpyrrolidone, Dichloromethane (all from Applied Biosystems/Perkin Elmer) and piperidine (Aldrich Chemical Co., St. Louis, Mo.), are used for synthesis reagents.

The Peptide Companion software (Peptides International, Louisville, Ky.) is used to predict the aggregation potential and difficulty level for synthesis for the zdint-1 peptide. Synthesis is performed using single coupling programs, according to the manufacturer's specifications.

The peptide is cleaved from the solid phase following standard TFA cleavage procedure (according to Peptide Cleavage manual, Applied Biosystems/Perkin Elmer). Purification of the peptide is done by RP-HPLC using a C18, 10 µm semi-peparative column (Vydac, Hesperial, Calif.). Eluted fractions from the column are collected and analyzed for correct mass and purity by electrospray mass spectrometry. Pools of the eluted material are collected. If pure, the pools are combined, frozen and lyophilized.

Example 6

Anticoagulant Activity of Zdint1

The ability of the zdint1 protein to inhibit clotting is measured in a one-stage clotting assay using wild-type zdint1 as a control. Recombinant proteins are prepared essentially as described above from cells cultured in media containing 5 mg/ml vitamin K. Varying amounts of the zdint1 or recombinant wild-type zdint1 are diluted in 50 mM Tris pH 7.5, 0.1% BSA to 100 ml. The mixtures are incubated with 100 ml of zdint1-deficient plasma and 200 ml of thromboplastin C (Dade, Miami, Fla.; contains rabbit brain thromboplastin and 11.8 mM $Ca^{++}$). The clotting assay is performed in an automatic coagulation timer (MLA Electra 800, Medical Laboratory Automation Inc., Pleasantville, N.Y.), and clotting times are converted to units of zdint1 activity using a standard curve constructed with 1:5 to 1:640 dilutions of normal pooled human plasma (assumed to contain one unit per ml zdint1 activity; prepared by pooling citrated serum from healthy donors).

Zdint1 activity is seen as a reduction in clotting time over control samples.

Example 7

Inhibition of Platelet Accumulation with Zdint1

Zdint1 is analyzed for its ability to inhibit platelet accumulation at sites of arterial thrombosis due to mechanical injury in non-human primates. A model of aortic endarterectomy is utilized in baboons, essentially as described by Lumsden et al. (*Blood* 81: 1762–1770 (1993)). A section of baboon aorta 1–2 cm in length is removed, inverted and scraped to remove the intima of the artery and approximately 50% of the media. The artery is reverted back to its correct orientation, cannulated on both ends and placed into an extracorporeal shunt in a baboon, thereby exposing the mechanically injured artery to baboon blood via the shunt. Just prior to opening of the shunt to the circulating blood, $^{111}$In-labeled autologous platelets are injected intravenously into the animal. The level of platelet accumulation at the site of the injured artery is determined by real-time gamma camera imaging.

Evaluation of zdint1 for inhibition of platelet accumulation is done using bolus injections of zdint1 or saline control and are given just prior to the opening of the shunt. The injured arteries are measured continuously for 60 minutes.

Zdint1 activity is seen as an inhibition of platelet accumulation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An isolated polynucleotide molecule encoding a polypeptide molecule, wherein the polypeptide molecule comprises residues 383 to 464 of SEQ ID NO:2 and wherein the polypeptide molecule binds an integrin.

2. The isolated polynucleotide molecule according to claim 1, wherein the polypeptide molecule comprises residues 383 to 696 of SEQ ID NO:2 and wherein the polypeptide molecule binds an integrin.

3. An isolated polynucleotide encoding a polypeptide wherein the amino acid sequence of the polypeptide is residues 164 to 464 of SEQ ID NO:2 and wherein the polypeptide molecule binds an integrin.

4. The isolated polynucleotide of claim 1 wherein the polypeptide molecule comprises the amino acid sequence as shown in SEQ ID NO:2 from residue 164 to 696 of SEQ ID NO:2 and wherein the polypeptide molecule binds an integrin.

5. The isolated polynucleotide molecule according to claim 2, wherein the polypeptide molecule comprises residues 1 to 696 of SEQ ID NO:2.

6. An isolated polynucleotide selected from the group consisting of:
   a) the polynucleotide as shown in SEQ ID NO:1; and
   b) the polynucleotide that is complementary to a).

7. An expression vector comprising the following operably linked elements:
   a) a transcription promoter;
   b) a DNA segment comprising a polynucleotide according to claim 1; and
   c) a transcription terminator wherein the DNA segment encodes a polypeptide and wherein the polypeptide binds an integrin.

8. The expression vector of claim 7 wherein the DNA segment further encodes an affinity tag.

9. A cultured cell into which has been introduced the expression vector according to claim 7, wherein said cell expresses the polypeptide encoded by the DNA segment.

10. A method of producing a polypeptide comprising culturing the cell according to claim 9, whereby said cell expresses the polypeptide encoded by the DNA segment; and recovering the polypeptide.

* * * * *